United States Patent
Payonk et al.

(10) Patent No.: US 8,026,942 B2
(45) Date of Patent: Sep. 27, 2011

(54) SKIN IMAGING SYSTEM WITH PROBE

(75) Inventors: Gregory Payonk, Flanders, NJ (US);
Georgios Stamatas, Somerset, NJ (US);
Nikiforos Kollias, Skillman, NJ (US)

(73) Assignee: Johnson & Johnson Consumer Companies, inc., Skillman, NJ (US)

( * ) Notice: Subject to any disclaimer, the term of this patent is extended or adjusted under 35 U.S.C. 154(b) by 1561 days.

(21) Appl. No.: 11/169,813

(22) Filed: Jun. 29, 2005

(65) Prior Publication Data

US 2006/0092315 A1   May 4, 2006

Related U.S. Application Data

(63) Continuation-in-part of application No. 10/978,284, filed on Oct. 29, 2004, now Pat. No. 7,738,032.

(51) Int. Cl.
*H04N 7/18* (2006.01)
*A61B 5/00* (2006.01)

(52) U.S. Cl. .......................... 348/77; 600/306

(58) Field of Classification Search ............ 348/370, 348/77, 65, 14.06, 14.08, 14.09, 371, 360, 348/333.12, 207.1, 159, 231, 231.99; 382/170, 382/181, 195, 190, 206, 225, 205, 159, 128; 606/9, 10; 396/14, 661, 15; 600/160, 104, 600/106, 111, 101, 102, 109, 112, 306, 309, 600/310, 131, 153, 159, 125, 114, 121, 136, 600/407, 476, 167, 179, 129
See application file for complete search history.

(56) References Cited

U.S. PATENT DOCUMENTS 3,353,884 A   11/1967   Chaffee et al.
3,904,283 A   9/1975   Arai (Continued)

FOREIGN PATENT DOCUMENTS

EP   682236 A1   11/1995

(Continued)

OTHER PUBLICATIONS

Gartstein et al., "Assessment of Visual Signs of Skin Aging", Bioengineering of the Skin: Skin Surface Imaging and Analysis, edited by K. P. Wilhelm et al., Chapter 3, CRC Press, Inc. (1997) pp. 331-344 (10 pages).

(Continued)

*Primary Examiner* — Behrooz Senfi

(57) ABSTRACT

A skin testing and imaging station and corresponding method for capturing, displaying and analyzing images of a person and for testing the skin using a variety of probes includes a digital camera, a light source capable of providing at least two different wavelengths of light, a plurality of probes for conducting skin tests, a touch-screen display and a computer for controlling the components of the station. The apparatus selectively captures and displays a plurality of digital images using different wavelengths of illuminating light, e.g., using a plurality of flashes and filters, some of which may be adjustable to adjust the angle of incidence of the illuminating light on the subject. In video mode, the camera displays a real time image on the display facilitating a user to position a probe for testing any specific area of the skin. Preferably, the apparatus is self-serve, allowing any person to capture, review and analyze the images and skin data. Verbal and/or graphic instructions to a user aid in use of the station. An intuitive graphic user interface with thumbnail images is employed. Focus control, zoom and synchronized side-by side comparison of images are available.

18 Claims, 16 Drawing Sheets

U.S. PATENT DOCUMENTS

| | | |
|---|---|---|
| 3,904,293 A | 9/1975 | Gee |
| 4,170,987 A | 10/1979 | Anselmo et al. |
| 4,398,541 A | 8/1983 | Pugliese |
| 4,842,523 A | 6/1989 | Bourdier et al. |
| 4,905,700 A | 3/1990 | Wokalek et al. |
| 4,911,544 A | 3/1990 | Walsh |
| 5,005,975 A | 4/1991 | Kawai et al. |
| 5,016,173 A | 5/1991 | Kenet et al. |
| 5,198,875 A | 3/1993 | Bazin et al. |
| 5,241,468 A | 8/1993 | Kenet |
| 5,363,854 A | 11/1994 | Martens et al. |
| 5,408,996 A * | 4/1995 | Salb ............................ 600/317 |
| 5,456,260 A | 10/1995 | Kollias et al. |
| 5,556,612 A | 9/1996 | Anderson et al. |
| 5,640,957 A | 6/1997 | Kaminski et al. |
| 5,742,392 A | 4/1998 | Anderson et al. |
| 5,760,407 A | 6/1998 | Margosiak et al. |
| 5,827,190 A | 10/1998 | Palcic et al. |
| 5,828,793 A | 10/1998 | Mann |
| 5,836,872 A | 11/1998 | Kenet et al. |
| 5,943,603 A | 8/1999 | Parulski et al. |
| 5,973,779 A | 10/1999 | Ansari et al. |
| 5,991,433 A | 11/1999 | Osanai et al. |
| 6,018,586 A | 1/2000 | Kamei |
| 6,032,071 A | 2/2000 | Binder |
| 6,076,904 A | 6/2000 | Shepherd et al. |
| 6,081,612 A | 6/2000 | Gutkowicz-Krusin et al. |
| 6,134,011 A | 10/2000 | Klein et al. |
| 6,148,092 A | 11/2000 | Qian |
| 6,208,749 B1 * | 3/2001 | Gutkowicz-Krusin et al. ............................ 382/128 |
| 6,215,893 B1 | 4/2001 | Leshem et al. |
| 6,224,542 B1 * | 5/2001 | Chang et al. ................. 600/109 |
| 6,251,070 B1 | 6/2001 | Khazaka |
| 6,278,999 B1 | 8/2001 | Knapp |
| 6,293,284 B1 | 9/2001 | Rigg |
| 6,317,624 B1 | 11/2001 | Kollias et al. |
| 6,352,502 B1 | 3/2002 | Chaiken et al. |
| 6,436,127 B1 | 8/2002 | Anderson et al. |
| 6,437,856 B1 | 8/2002 | Jacques |
| 6,441,854 B2 | 8/2002 | Fellegara et al. |
| 6,505,059 B1 | 1/2003 | Kollias et al. |
| 6,507,747 B1 | 1/2003 | Gowda et al. |
| 6,537,211 B1 | 3/2003 | Wang et al. |
| 6,571,003 B1 | 5/2003 | Hillebrand et al. |
| 6,592,882 B2 | 7/2003 | George et al. |
| 6,597,392 B1 | 7/2003 | Jenkins et al. |
| 6,600,947 B2 | 7/2003 | Averback et al. |
| 6,603,552 B1 | 8/2003 | Cline et al. |
| 6,619,860 B1 | 9/2003 | Simon |
| 6,624,843 B2 | 9/2003 | Lennon |
| 6,681,133 B2 | 1/2004 | Chaiken et al. |
| 6,711,426 B2 | 3/2004 | Benaron et al. |
| 6,721,582 B2 | 4/2004 | Trepagnier et al. |
| 6,728,560 B2 | 4/2004 | Kollias et al. |
| 6,790,179 B2 | 9/2004 | Skover |
| 6,961,517 B2 * | 11/2005 | Merola et al. .................... 396/14 |
| 7,349,857 B2 | 3/2008 | Manzo |
| 7,376,346 B2 * | 5/2008 | Merola et al. .................... 396/14 |
| 7,413,567 B2 | 8/2008 | Weckwerth et al. |
| 2001/0013897 A1 | 8/2001 | Kowno et al. |
| 2002/0049432 A1 * | 4/2002 | Mukai ............................... 606/9 |
| 2002/0059030 A1 | 5/2002 | Otworth et al. |
| 2002/0065468 A1 | 5/2002 | Utzinger et al. |
| 2002/0071246 A1 | 6/2002 | Stewart |
| 2002/0161664 A1 | 10/2002 | Shaya et al. |
| 2002/0181752 A1 | 12/2002 | Wallo et al. |
| 2002/0182235 A1 | 12/2002 | Slavtcheff et al. |
| 2003/0045916 A1 | 3/2003 | Anderson et al. |
| 2003/0067545 A1 | 4/2003 | Giron et al. |
| 2003/0086703 A1 | 5/2003 | Kollias et al. |
| 2003/0086712 A1 | 5/2003 | Merola et al. |
| 2003/0108542 A1 | 6/2003 | Pruche et al. |
| 2003/0138249 A1 | 7/2003 | Merola et al. |
| 2003/0191379 A1 | 10/2003 | Benaron et al. |
| 2004/0061776 A1 * | 4/2004 | Mochida et al. ................. 348/65 |
| 2004/0077951 A1 | 4/2004 | Lin et al. |
| 2004/0125996 A1 * | 7/2004 | Eddowes et al. ............... 382/128 |
| 2004/0136002 A1 * | 7/2004 | Whaite et al. .................. 356/419 |
| 2004/0146290 A1 | 7/2004 | Kollias et al. |
| 2004/0258304 A1 * | 12/2004 | Shiota et al. ................... 382/170 |
| 2005/0131304 A1 | 6/2005 | Stamatas et al. |
| 2005/0146863 A1 | 7/2005 | Mullani |
| 2005/0201935 A1 | 9/2005 | Merola et al. |
| 2006/0268148 A1 | 11/2006 | Kollias et al. |

FOREIGN PATENT DOCUMENTS

| | | |
|---|---|---|
| EP | 737932 A2 | 10/1996 |
| EP | 1089208 A2 | 4/2001 |
| EP | 1118845 A2 | 7/2001 |
| EP | 1194898 B1 | 3/2003 |
| EP | 1297782 | 4/2003 |
| EP | 1433418 | 6/2004 |
| EP | 1541084 | 6/2005 |
| FR | 2821152 A1 | 8/2002 |
| GB | 2106241 A | 4/1983 |
| GB | 2293648 | 4/1996 |
| JP | 7075629 A | 3/1995 |
| JP | 7323014 A | 12/1995 |
| WO | WO 94/24936 A1 | 11/1994 |
| WO | WO 9616698 | 6/1996 |
| WO | WO 97/05473 | 2/1997 |
| WO | WO 97/47235 A1 | 12/1997 |
| WO | WO 98/24360 A | 6/1998 |
| WO | WO 98/37811 A1 | 9/1998 |
| WO | WO 99/17668 | 4/1999 |
| WO | WO 00/76398 A1 | 12/2000 |
| WO | WO 01/04839 A2 | 1/2001 |
| WO | WO 01/22741 A2 | 3/2001 |
| WO | WO 01/22869 | 4/2001 |
| WO | WO 01/35827 A1 | 5/2001 |
| WO | WO 01/45557 A1 | 6/2001 |
| WO | WO 01/62788 A2 | 8/2001 |
| WO | WO 01/72216 | 10/2001 |
| WO | WO 01/82786 A2 | 11/2001 |
| WO | WO 02/061405 | 8/2002 |

OTHER PUBLICATIONS

Hillebrand, G., et al., "Quantitative evaluation of skin condition in an epidemiological survey of females living in northern versus southern Japan", Journal of Dermatological Science, 27 Suppl, 1 (2001) pp. S42-S52 (11 pages).

Kligman A., et al., "Ultraviolet Photography Serves as Both Predictor and Educator", Cosmetic Dermatology, vol. 10, No. 9 (1997) pp. 31-33 (3 pages).

Kollias, "Polarized Light Photography of Human Skin", Bioengineering of the Skin: Skin Surface Imaging and Analysis, Edited by K.P. Wilhelm et al., Chapter 7 (1997) pp. 95-104 (12 pages).

Kollias, N., et al., "Optical Non-Invasive Approaches to Diagnosis of Skin Diseases", Optical Diagnostics in Dermatology (2002) pp. 64-75 (12 pages).

Lucchina, L., et al., "Fluorescence photography in the evaluation of acne", Journal of the American Academy of Dermatology, vol. 35, No. 1, (1996) pp. 58-63 (6 pages).

Pagnoni A. et al., "Digtial fluorescence photography can assess the suppressive effect of benzoyl peroxide on Propionibacierium acnes", J. Am. Acad Dermatol, vol. 41, No. 5, Part 1, (1999) pp. 710-716 (7 pages).

Phillips, S, et al., "Polarized light photography enhances visualization of inflammatory lesions of acne vulgaris", Journal of the American Academy of Dermatology, vol. 37, No. 6, (1997) pp. 948-952 (5 pages).

European Search Report issued Apr. 21, 2009, in connection with European Patent Appln. No. 05 815 062.4 filed Oct. 28, 2005.

Kollias, et al., "Fluorescence Photography in the Evaluation of Hyperpigmentation in Photodamaged Skin", Journal of the American Academy of Dermatology, vol. 36, No. 2, Part 1, 1997, pp. 226-230.

Muccini, et al., "Polarized Light Photography in the Evaluation of Photoaging", Journal of the American Academy of Dermatology, vol. 33, Nov. 1995, pp. 765-769.

Anderson, "Polarized Light Examination and Photography of the Skin", Arch Dermatol, vol. 127, Jul. 1991, pp. 1000-1005.
European Search Report from Appln. No. EP 02 789 476.5.
Search Report from European Patent Appln. No. EP 06 25 3363.
"Apparatus and Method for Measuring Photodamage to Skin", U.S. Appl. No. 11/863,328, filed Sep. 28, 2007, Inventors: Gregory Payonk, et al.
"Imaging Station", U.S. Appl. No. 29/266,978, filed Oct. 2, 2006, Inventors: Masamichi Udagawa, et al.
"Imaging Apparatus and Methods for Capturing and Analyzing Digital Images of the Skin", U.S. Appl. No. 11/863,342, filed Sep. 28, 2007, Inventors: Jeffrey Pote, et al.
Excerpt from website: www.canfieldsci.com.
Z. Deyl, et al., "A Fluorescent Compound in Collagen and its Relation to the Age of the Animal", Exp. Geront., vol. 5, 1970, pp. 57-62.
Na, et al., "Autofluorescence of Human Skin is Age-Related After Correction for Skin Pigmentation and Redness", The Journal of Investigative Dermatology, vol. 116, No. 4, Apr. 2001, pp. 536-540.
Leffel, et al., "In Vivo Fluorescence of Human Skin", Arch Dermatol, vol. 124, Oct. 1998, pp. 1514-1518.
Anderson, "Correspondence: In Vivo Fluorescence of Human Skin", Arch Dermatol, vol. 125, Jul. 1989, pp. 999-1000.
Odetti, et al., "Age-Related Increase of Collagen Fluorescence in Human Subcutaneous Tissue", Department of Internal Medicine and the Department of Physics, University of Genova, Italy, 1992, pp. 655-658.
Sandby-Moller, et al., "Skin Autofluorescence as a Biological UVR Dosimeter", Photodermatol Photoimmunol Photomed, 2004, pp. 33-40.
Kollias, et al., "Endogenous Skin Fluorescence Includes Bands That May Serve as Quantitative Markers of Aging and Photoaging", The Society for Investigative Dermatology, Inc., vol. 111, No. 5, Nov. 1998, pp. 776-780.
Brancaleon, "The In Vivo Fluorescence of Tryptophan Moieties in Human Skin Increases with UV Exposure and is a Marker for Epidermal Proliferation", The Society for Investigative Dermatology, Inc., vol. 113, No. 6, Dec. 1999, pp. 977-982.
Taira, et al., "Aging and Effects of Ultraviolet A Exposure May be Quantified by Fluorescence Excitation Spectroscopy In Vivo", The Society for Investigative Dermatology, Inc., vol. 116, No. 6, Jun. 2001, pp. 840-845.
Barel, et al., "The Visi-Chroma VC-100®; A New Imaging Colorimeter for Dermatocosmetic Research", Skin Research and Technology, 7, 2001, pp. 24-31.
U.S. Appl. No. 11/170,129, Handheld Device for Determining Skin Age, Proliferation Status and Photodamage Level, filed Jun. 29, 2005.
U.S. Appl. No. 11/169,942, Apparatus and Method for Viewing the Skin, filed Jun. 29, 2005.
U.S. Appl. No. 10/978,284, Apparatus and Method of Taking and Viewing Images of the Skin, filed Oct. 29, 2004.
Georgios N. Stamatas, et al., "Non-Invasiuve Measurements of Skin Pigmentation in Situ", Pigment Cell Res. 17, 2004, pp. 618-626.
Nikiforos Kollias, et al., "Fluorescence Spectroscopy of Skin", Vibrational Spectroscopy 28, 2002, pp. 17-23.
George Zonios, et al., "Skin Melanin, Hemoglobin, and Light Scattering Properties Can be Quantitatively Assessed In Vivo Using Diffuse Reflectance Spectroscopy", The Journal of Investigative Dermatology, vol. 117, No. 6, Dec. 2001, pp. 1452-1457.
Georgios N. Stamatas, et al. "Blood Stasis Contributions to the Perception of Skin Pigmentation", Journal of Biomedical Optics, Mar./Apr. 2004, vol. 9., No. 2, pp. 315-322.
Robert Gillies, et al., "Fluorescence Excitation Spectroscopy Provides Information about Human Skin In Vivo", The Journal of Investigative Dermatology, vol. 115, No. 4, Oct. 2000, pp. 704-707.
Excerpts from website www.courage-khazaka.de, "Scientific Devices".
Excerpts from website www.novatechcorp.com.
Courage + Khazaka GmbH, "Studies List Reviscometer".

* cited by examiner

SKIN IMAGING SYSTEM WITH PROBE

CROSS-REFERENCES TO RELATED APPLICATIONS

This is a continuation in part of application Ser. No. 10/978,284, entitled Apparatus for and Method of Taking and Viewing Images of the Skin; filed Oct. 29, 2004 now U.S. Pat. No. 7,738,032 and owned by the assignee hereof.

FIELD OF THE INVENTION

The present invention relates to an apparatus and method for taking and viewing images of the skin, and more particularly for analyzing specific areas of the skin by obtaining measurements indicative of various condition states.

BACKGROUND OF THE INVENTION

In order to promote skin care products, many cosmetic companies ask their potential customers questions regarding perception of their skin. Based on the answers to these questions, cosmetic companies are able to better suggest cosmetic and therapeutic products to these people. Examples of such promotions can be found on the Internet WebPages of Neutrogena® (www.neutrogena.com), L'Oreal® (www.lorealparisusa.com), and Lancome® (www.lancome.com). These questions, however, are only based upon the subject's perception of their skin under visible light. Many skin problems, however, are not always visible under such conditions.

Various types of photography have been developed to enhance the visualization of the skin. In visible light photography, or standard photography, the most common arrangement includes a camera and one or more flash units to deliver visible light to the skin by direct illumination, diffuse illumination, or a combination thereof. Angled lighting has also been used to generate a gradient of the illuminating field on the skin in order to enhance the visualization of wrinkles and fine lines. Depending on the direction of the gradient (vertical or horizontal), different sets of wrinkles and fine lines may be visually enhanced.

Polarized light photography has also been developed to selectively enhance either surface or subsurface features of the skin. These results are accomplished by placing a polarizing filter (typically a linear polarizing filter) both in front of the flash unit, and in front of the camera. When the polarizing filters are in the same orientation with each other, surface features of the skin such as scales, wrinkles, fine lines, pores, and hairs are visually enhanced. When the polarizing filters are aligned perpendicular to each other, subsurface features of the skin such as erythema, pigmentation, blood vessels, and hair, are visually enhanced.

Ultraviolet photography, where the flash unit is filtered to produce ultraviolet A light and the camera is filtered so that only visible light enters the lens, has been used to visually enhance the appearance of pigmentation, the bacteria *p. acnes*, and horns. A variation of ultraviolet photography has been termed the "sun camera" where ultraviolet A light is used to illuminate the skin and an ultraviolet A sensitive film or a digital camera is used to record the reflected ultraviolet light from the skin. In this arrangement, both the pigment distribution and the surface features of the skin are visually enhanced.

In addition to apparatus for enhanced visualization of the skin, i.e., by viewing images captured by photography/videography, there are several other apparatus and methods known for testing various measurable parameters indicative of skin condition/attributes. For example, diffuse reflectance spectroscopy is known for use in determining the concentration of skin chromophores, melanin, oxy-hemoglobin and deoxy-hemoglobin, porphyrins and bilirubin viz., by observing the absorption spectra. Fluorescence spectroscopy is similarly useful for ascertaining the presence of tryptophan, collagen cross-links, elastin cross-links and keratin. The elasticity of the skin can be measured by an apparatus commercially known as a Reviscometer®. Skin surface hydration can be measured by an apparatus commercially known as a Corneometer® and the conductivity of the skin can be measured by a NovaMeter®. Typically, these known apparatus for measuring skin attributes are provided for use by professionals and are not intended for consumer use.

The present invention provides people with access to one or more of these improved means of viewing and testing their skin, in order to provide them additional insight into the condition of their skin. Such insight allows them to make more informed decisions regarding the purchase of skin care products. In addition, skin care products can be suggested to such potential customers by retailers or professionals based upon such customer's enhanced perception of their skin.

SUMMARY OF THE INVENTION

The problems and disadvantages associated with conventional apparatus and techniques utilized to capture data about a person's skin are overcome by the present invention, which includes a camera for capturing the images of the person, a display for displaying images captured by the camera, at least one probe for measuring a predetermined parameter of the skin in a specific area; a controller for controlling the camera, the probe and the display for selectively capturing images of the person and skin data from the probe and displaying the captured images and skin data on the display.

In accordance with a method of the invention, an imaging station having a camera, a light source, a display mounted for displaying images captured by the camera, at least one probe for measuring a parameter of the skin in a specific area and a controller with an operator interface is provided. The person whose image is to be captured is positioned relative to the camera and given the option of capturing images with the camera and/or obtaining skin data with the probe. The captured images and/or skin data are stored and selectively displayed on the display.

Other aspects, features, and advantages of the present invention will be apparent from the detailed description of the invention and from the claims.

DETAILED DESCRIPTION OF THE INVENTION

Figure 1:
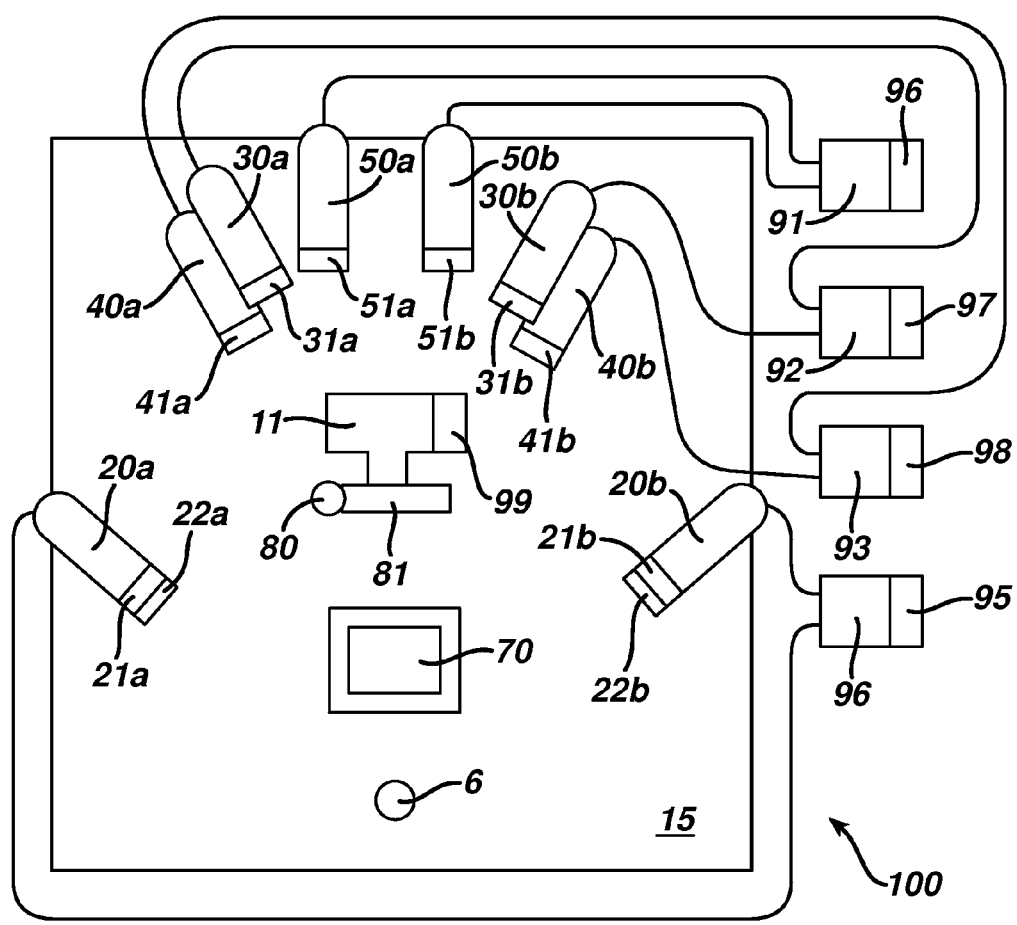
FIG. 1 is an overhead view of an apparatus used to sequentially take the following four types of pictures of a person: a standard photograph, a polarized photograph, an ultraviolet A photograph, and a blue fluorescence photograph.

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

The Camera

Various types of cameras may be used in the methods of the present invention. Examples of such cameras include, but are not limited to, standard 35 mm cameras, cameras using instant developing film (such as those available from Polaroid Corporation, Cambridge, Mass. USA), and digital cameras. Preferably, a digital camera is used as it provides fast access to the images taken of the subject. It also allows the image to be displayed on a large monitor, enables the subject to easily enlarge areas of skin that are of particular interest (e.g., areas of the face), and allows the image to be printed in a report which can also include suggestions for products addressing any concerns the subject noticed upon examining the images. Examples of suitable digital cameras include, but are not limited to, those which take images of at least 1 million pixels, preferable at least 4 million pixels. Examples of such digital cameras include, but are not limited to, the Nikon D1X (Nikon, Tokyo, Japan) and the Fuji S1 (Fuji, Tokyo, Japan).

One or more cameras may also be used in the methods of the present invention, e.g., separate cameras having a distinct light filtering lens may be used for each type of photograph taken and/or separate cameras used to photograph different areas or angles of the subject. Preferably, only one camera is used since having more than one camera would require that the cameras be calibrated to have the same color and intensity response. When only one camera is used, a mechanical filter wheel or arm containing a filter(s) may be placed in front of the camera to selectively filter the light prior to or after entering the camera's lens and/or the respective filter(s) may be placed at the light source(s) to filter the light as it leaves the light source(s). In the case where multiple light sources are used, the camera can communicate with each of the respective light sources via hard wiring or a radio transceiver.

In one embodiment, the camera(s) are mounted at the same level as the area of skin that the subject desires to be photographed, e.g., the face of the subject. Preferably, the camera is set such that such area of skin substantially fills the frame area of the photograph, e.g., to ensure the greatest amount of detail in the image.

In one embodiment where multiple images are acquired by single camera, the images are preferably acquired in less than about 30 seconds, e.g., less than about 10 seconds.

Standard Photography

In one embodiment, the method includes the step of taking a standard photograph of the subject. What is meant by "standard photograph" is a photograph that is taken of the subject using visible light (e.g., light having a wavelength from about 400 to about 700 nm). In one embodiment, the subject is illuminated with one or more, preferably two, flash units that emit visible light. In one embodiment, the flash unit(s) are further equipped with a diffusing filter that is placed in front of each flash unit. A diffusing filter is a filter, which assists in uniformly dispersing light (e.g., to help eliminate "hot spots"). Examples of such diffusing filters include, but are not limited to, frosted glass filters such as a Broncolor Diffuser (Sinar Bron, Allschwil, Switzerland), metal grids which may be printed on glass substrates, or a diffusing reflective umbrella for indirect lighting.

In one embodiment, the flash unit(s) are angled at the subject's skin to generate a gradient across the surface of the skin. In a further embodiment, the flash units are mounted higher than the skin area of the subject and aimed at such skin area in order to give a gradient of light on the skin from the top to the bottom. In one embodiment, the angle of the flash units is from about 5 to about 30 degrees, such as about 10 degrees, from horizontal. This gradient visually enhances various features of the skin such as the fine lines and wrinkles in the subject, e.g., the crow's feet around the eye and forehead or mouth area wrinkles.

Polarized Light Photography

In one embodiment, the method includes the step of taking a polarized photograph of the subject. What is meant by "polarized photograph" is a photograph of the subject taken (i) with a light source that emits light through a polarizing filter and/or (ii) through a polarized filter that filters light prior to or after entering the camera's lens.

In one embodiment, the camera and one or more flash units, preferably two, are on about the same plane as the subject's skin to be photographed, and the flash units are placed so that the angle formed by each flash unit(s), subject's skin, and camera is about 35 to 55 degrees, such as about 45 degrees. In one embodiment, a polarizing filter is placed in front of each flash unit. What is meant by a "polarizing filter" is a filter that filters incoming light to emit substantially only polarized light. What is meant by the term "substantially," as used herein, is at least 75 percent, preferably 90 percent, and most preferably at least 95 percent.

Examples of a polarizing filter include, but are not limited to, polarizing plates such as those available from Edmund Scientific (Barrington, N.J. USA), polarizing prisms such as Glan Thomson polarizing prisms, or a polarizing reflector that reflects light at about the Brewster angle. Polarizing filters may be linear or circular polarizing filters. In a further embodiment, a light diffuser is placed between the flash unit and the polarizing filter.

In one embodiment, a linear polarizing filter is used at the light source and the linear polarizing filter is arranged such that the electric field of the emitted light is about perpendicular to the plane formed by the light source, the person's skin, and the camera. In another embodiment, a linear polarizing filter is used at the light source and the linear polarizing filter is arranged such that the electric field of the emitted light is about parallel to the plane formed by the light source, the person's skin, and the camera.

In a further embodiment, the flash unit(s) are positioned on a horizontal plane with the camera and the subject's skin and the polarizing filter is a linear polarizing filter oriented so that the electric field of the transmitted light is in the vertical direction (e.g., perpendicular to the plane). In this orientation, the critical angle for total internal reflection from within the top corneocytes is 45 degrees, thereby resulting in an image that is dominated by the light thus reflected from the corneocytes. The resulting image has a high degree of glare, which is further enhanced when an optical coupling medium, such as sebum or "oils," is present on the surface of the corneocytes. The polarized image, thereby, allows an estimate to be made as to the oiliness of the subject's skin. It also provides insight into the number and severity of pores on the cheek and forehead areas of the facial skin. Other desired outcomes of polarized photography include, but are not limited to, an enhanced image of surface features such as fine lines, skin texture, scales and vellous hair.

In another embodiment, the flash unit(s) are positioned on a vertical plane above the camera and the subject's skin so that the angle formed by the flash unit, subject's skin, and camera is about 35 to 55 degrees such as about 45 degrees and flash unit(s) are filtered with linear polarizing filter that is placed with the transmitted electric field in the vertical direction (e.g., parallel to the plane). In this arrangement the surface glare from the skin is minimized, thus, enhancing the subsurface features of the skin, such as erythema (redness), blood vessels, and pigmentation.

Polarized light sources on both on the horizontal and vertical planes with the camera and the subject's skin can be used to enhance specific aspects of the skin (e.g., the face) that are partially shaded with the use of polarized light sources only on the horizontal or vertical planes alone.

In one embodiment, the photograph of the subject is taken both with a light source that emits lights through a polarizing filter and through a polarizing filter that filters the light prior to or after entering the camera's lens. When the polarizing filters are in the same orientation with each other (e.g., both horizontal or both vertical), surface features of the skin such as scales, wrinkles, fine lines, pores, and hairs are visually enhanced. When the polarizing filters are aligned perpendicular to each other (e.g., one horizontal and one vertical), subsurface features of the skin such as erythema, pigmentation, blood vessels, and hair, are visually enhanced.

Ultraviolet Imaging

In one embodiment, the method includes the step of taking an "ultraviolet photograph" of the subject. What is meant by "ultraviolet photograph" is a photograph of the subject taken (i) with a light source that either emits substantially only ultraviolet light (radiation) or emits light through an ultraviolet filter and/or (ii) through an ultraviolet filter that filters the light prior to or after entering the camera's lens. What is meant by an ultraviolet filter is a filter that filters incoming light to emit substantially only ultraviolet light (e.g., light having a wavelength from about 200 to about 400 nm). Examples of light sources that can emit substantially only ultraviolet light are light emitting diodes. Examples of ultraviolet imaging include, but are not limited to, ultraviolet A imaging or ultraviolet B imaging.

Ultraviolet A Imaging

In one embodiment, the method includes the step of taking an "ultraviolet A photograph" of the subject. What is meant by "ultraviolet A photograph" is a photograph of the subject taken (i) with a light source that emits substantially only ultraviolet A light or emits light through an ultraviolet A filter and/or (ii) through an ultraviolet A filter that filters the light prior to or after entering the camera's lens.

In one embodiment, one or more, preferably two, flash units are filtered with an ultraviolet A filter ("UVA filter"). What is meant by a UVA filter is a filter that filters incoming light to emit substantially only light having a wavelength of from about 320 to about 400 nm. Examples of UVA filters include, but are not limited to, the ultraviolet UG-11 filter (Schott Glass Technologies, Duryea, Pa. USA). The resulting image may be rich in red color because of the long wavelength pass of UVA filter. In one embodiment, when utilizing a digital camera, either the blue or green channel, preferably the blue channel, of the RGB image is selected for viewing, resulting in a black and white image.

Benefits of an ultraviolet A photograph include, but are not limited to, enhanced appearance of pigmented macules on the skin and surface features such as bumps and wrinkles. Ultraviolet A imaging may be used to determine the uniformity of application of topical products, such as sunscreens and of make-ups, that contain materials that absorb ultraviolet radiation. In addition, since melanin pigmentation more strongly absorbs UVA radiation than visible light, illuminating the skin with UVA radiation gives an enhanced contrast between normal skin and hyper pigmented skin. Furthermore, the pigmented macules are visualized as dark spots on a bright background due to the scattering and the fluorescence of the dermal collagen matrix. The image recorded by the camera includes both the reflection of ultraviolet A radiation and fluorescence of the collagen. The resulting black and white image obtained by the blue or green channel from a digital camera provides an enhanced view of the distribution of pigmented macules on the skin (e.g., the face). For subjects with deeply pigmented skin, the red channel may be selected.

In another embodiment, the flash units are further filtered with a red blocking filter. Examples of such red blocking filter include, but is not limited to, a KG-5 filter (Schott Glass Technologies). Such filters may assist in correcting the red appearance of the image.

Blue Fluorescence Imaging

In one embodiment, the method includes the step of taking a "blue fluorescence photograph" of the subject. What is meant by "blue fluorescence photograph" is a photograph of the subject taken with a light source that emits substantially only blue light or emits light through a blue filter. What is meant by "blue light" is light having a wavelength from about 380 to about 430 nm.

In one embodiment, one or more, preferably two, flash units are filtered with a blue filter. What is meant by a "blue filter" is a filter that filters incoming light to emit substantially only blue light. Examples of such blue filters include, but are not limited to, interference filters such as those available from Melles Griot (Irvine, Calif. USA) or dielectric filters.

In one embodiment, the light entering the camera is also filtered (e.g., prior to or after entering the lens of the camera) with a long pass filter to substantially eliminate light having a wavelength below about 400 nm. Examples of long pass filters include, but are not limited to, GG-420 or GG-440 filters (Schott Glass Technologies) and Kodak Wratten No. 8 (Eastman Kodak, Rochester, N.Y. USA). In one embodiment, the flash units and filters are placed on either side of the camera at approximately the same horizontal plane as the skin sample of the subject.

This type of imaging produces bright images of the distribution of coproporphyrin produced by the bacteria *P. acnes* and of horns. What is meant by a "horn" is a mixture of sebaceous lipids, keratinocytes, and possibly sebocytes impacted in open comedones and blackheads on the skin. By using substantially only blue light that is within the Soret absorption band of porphyrins, the fluorescence emission of coproporphyrin is maximized. Excitation in this range also yields bright emission images of the distribution of "horns" because the fluorescence yield of horns is higher when excited in the blue region of the spectrum.

In one embodiment, when utilizing a digital camera, the color image may be viewed showing the distribution of coproporphyrin and therefore the sites of maximum *p. acnes* concentration, which appears red in the image. The image also contains bright white spots, which correspond to clogged pores or open comedones. In another embodiment the green channel of the RGB image is selected to enhance the horn fluorescence emission and the red channel may be selected to enhance the fluorescence emission of porphyrins from *p. acnes*. The resulting black and white images, thus, provide excellent imaging of small vessels because hemoglobin has its Soret band in the same wavelength range as porphyrins. In one embodiment, these vessels are visualized using either the blue or the green channel of the RGB image.

Promotion of Skin Care Products

Upon acquisition of the photographs, these images are presented to the subject. The means of presenting the photographs depends in part on the type of photograph taken (e.g., using standard film, instant developing film, or a digital image). When using standard film or instant developing film, the prints of the images are provided to the subject. The prints may also be scanned and presented to the subject on a computer monitor (e.g., a LCD or CRT monitor). When using a digital camera, the image may also be presented on such a monitor.

Following presentation of the images to the subject, skin care products can be suggested to the person based upon his/her review of the images. In one embodiment, the method comprises presenting the subject with one or more questions relating to the presented images. Based upon the answers to such questions, one or more skin care products can be suggested to the subject. These products can be associated with responses to the questionnaire, made by a person reviewing the subject's answers, or made by a computer based upon the answers of the subject. The review of the various images by the subject facilitates more informed answers to the questions.

In one embodiment, the suggestions of skin care products is made by a computer program that recommends products based upon the answers provided by the subject.

In one embodiment, a list of skin care products are maintained on a relational database. These products are associated with answers to certain questions. Thus, based upon the answers provided by the subject, certain products are selected by the computer program. For example, if the subject answers that he/she has wrinkles, the computer program will search the data based for skin care products effective for treating wrinkles (e.g., products containing retinol) and/or if the subject answers that he/she has acne, the computer program will search the database for skin care products effective for treating acne (e.g., products containing benzoyl peroxide or salicylic acid).

In one embodiment, these suggestions are limited to a set number of products, e.g., the program will not recommend more than five products. In such a case, the computer program will prioritize skin care product suggestions based upon either the importance of the skin disorders identified by the subject or the database's ranking of importance of the skin disorder to be addressed. For example, if the subject responds that he/she has severe acne and moderate fine lines, the computer program will recommend acne product(s).

In one embodiment, following application of a skin care product (e.g., one suggested by the present method) for a period of time (e.g., one week, one month, or one year), the subject is then photographed again. These new photographs are compared to the original photographs to determine the efficacy of the skin care product.

In one embodiment, the recommended products may be available at the location where the photographs are taken, e.g., the photographs are taken in a store or kiosk that sells skin care products.

Skin Care Product

Following the subject's visual analysis of the images, skin care product(s) can be suggested to the subject to address any perceived problems identified following such analysis.

What is meant by a "skin care product" is a topical composition comprising cosmetically active agent. What is meant by a "cosmetically active agent" is a compound (e.g., a synthetic compound or a compound isolated from a natural source) that has a cosmetic or therapeutic effect on the skin, including, but not limiting to, anti-aging agents, lightening agents, darkening agents such as self-tanning agents, anti-acne agents, shine control agents, anti-microbial agents, anti-inflammatory agents, anti-mycotic agents, anti-parasite agents, sunscreens such as UVA/UVB blocking or absorbing agents, photo protectors, antioxidants, keratolytic agents, detergents/surfactants, astringents, moisturizers, nutrients, amino acids, amino acid derivatives, minerals, plant extracts, animal-derived substances, vitamins, energy enhancers, anti-perspiration agents, astringents, deodorants, hair removers, hair growth stimulators, hair growth retarding agents, firming agents, anti-callous agents, and agents for nail and/or skin conditioning.

In one embodiment, the cosmetically-active agent is selected from, but not limited to, the group consisting of hydroxy acids, benzoyl peroxide, sulfur resorcinol, ascorbic acid, D-panthenol, hydroquinone, octyl methoxycinnimate, titanium dioxide, octyl salicylate, homosalate, avobenzone, polyphenolics, carotenoids, free radical scavengers, retinoids such as retinoic acid, retinol, and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera, witch hazel, and legumes such as soy beans, and derivatives and mixtures thereof. The cosmetically active agent will typically be present in the composition of the invention in an amount of from about 0.001% to about 20% by weight of the composition, e.g., about 0.01% to about 10% such as about 0.1% to about 5%.

Examples of vitamins include, but are not limited to, vitamin A, vitamin Bs such as vitamin B3, vitamin B5, and vitamin B12, vitamin C, vitamin K, and vitamin E and derivatives thereof.

Examples of hydroxy acids include, but are not limited, to glycolic acid, lactic acid, malic acid, salicylic acid, citric acid, and tartaric acid.

Examples of antioxidants include but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, glutathione, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis.

Various other cosmetically-active agents may also be present in the skin care products. These include, but are not limited to, skin protectants, humectants, and emollients. The skin care products may also comprise chelating agents (e.g., EDTA), preservatives (e.g., parabens), pigments, dyes, opacifiers (e.g., titanium dioxide), and fragrances.

The following is an example of a manner of practicing a method of the present invention. Other manners may be practiced by those of ordinary skill in the art.

EXAMPLE

One embodiment of the present invention utilizes a kiosk that is intended to be an interactive tool from which subjects (e.g., potential customers) can evaluate their facial skin and decide upon a course of action to improve the appearance of the skin. The kiosk is designed such that a subject will have a series of images acquired of their face and the images will be presented to them one at a time along with questions relating to the displayed images.

In one example of the present invention, the kiosk comprises apparatus 100, as set forth in FIG. 1 (not to scale). Apparatus 100 is enclosed above and on three side (the side containing chin rest 6 in open for the subject to enter his/her head) with a frosted plastic glass (not shown). Apparatus 100, which is capable of taking four types of photographs of the subject, is set-up on table 15 having dimensions of 30" by 36". Half way along the long dimension of table 15 (about 18" from one end) and about 1⅝" in from the front end of table 15 there is chin rest 6 for the subject's chin. The height of chin rest 6 is about 12" above table 15. Across from chin rest 6 and exactly half way along the opposite end of the table 15 is camera 11 (Nikon D1X). Camera 11 is mounted so that the center of the camera lens of camera 11 is about 17" above the top of table 15. The distance between chin rest 6 and the front end of the lens of camera 11 is adjusted so that the subject's face substantially fills the camera frame of camera 11.

On the side of table 15 away from chin rest 6 are flash units 30a, 30b, 40a, 40b, 50a, and 50b (Broncolor Picolites, Sinar Bron, Allschwil, Switzerland) which are powered, respectively, by power packs 92, 92, 93, 93, 91, and 91. The standard flash units 50a and 50b, which are used for taking a standard photograph, are mounted above camera 10 and angled down about 20 degrees. Flash units 50a and 50b are directed toward the center of the subject's face. Diffusing filters 51a and 51b (Broncolor Diffuser, Sinar Bron) are placed, respectively, in front of flash units 50a and 50b.

UVA flash units 30a and 30b, which are used for the ultraviolet A photography, are mounted on either side of camera 11 at about 14" from the edge of table 15 and at a height of about 20" from the top of table 15. UVA filters 31a and 31b (UG-11 filters, Schott Glass Technologies, Duryea, Pa. USA) are placed, respectively, in front of UVA flash units 30a and 30b. Blue flash units 40a and 40b, which are used for blue fluorescence photography, are also mounted on either side of the camera at about 14" from the edge of the table top and at a height of about 13" from the top of table 15. Blue filters 41a and 41b (Melles Griot, Irvine, Calif. USA) are placed, respectively, in front of blue flash units 40a and 40b. The UVA flash units 30a and 30b and the blue flash units 40a and 40b are directed to the center of the face of the subject.

The polarized flash units 20a and 20b (Broncolor Picolites), which are used for polarized light photography, are powered by power pack 90. Diffusing filters 21a and 21b (Broncolor Diffuser, Sinar Bron) are placed, respectively, in front of polarized flash units 20a and 20b, respectively. Linear polarizing filters 22a and 22b (Edmund Scientific, Barrington, N.J. USA) are placed, respectively, in front of diffusing filters 21a and 21b in a vertical orientation. Polarized flash unit 20a is positioned at about 4½" from the left edge and about 14" in from the proximal edge of table 15 and polarized flash unit 20b is positioned at about 4½" from the right edge and about 14" in from the proximal edge of table 15. The angle between either flash units 20a or 20b, the chin rest 6, and the camera 11 is about 45 degrees.

The method begins when the subject enters the kiosk image acquisition area and enters basic demographic information into a facial skin-care evaluation computer program (Microsoft Visual Basic, Microsoft Corporation, Redmond, Wash. USA) using a touch-screen monitor 70 (SecurePoint, SeePoint Technologies, Torrance, Calif.), which is mounted under table 15 and connected to the same computer running the computer program. The subject enters data into the computer program via monitor 70 (computer program runs MountFocus Runtime Keyboard and the keyboard present on monitor 70 was designed using MountFocus Keyboard designer programs (MountFocus Information Systems, Wilmington, Del. USA)), however, other input device such as a keyboard, a track ball, and a computer mouse may be used. Examples of such information include, but are not limited to, age and gender of the subject. Following the input of such demographic information, the computer program then instructs the subject to place their chin on chin rest 6 and indicates to the subject to close his/her eyes since apparatus 100 is ready to take photographs.

Upon touching monitor 70, the software makes a function call to an image acquisition and display software ("IDL software"; IDL, Research Systems, Inc., Boulder, Colo.) running on the same computer. The IDL software then triggers camera 11 to acquire a blue fluorescence photograph, a standard photograph, a polarized photograph, and an ultraviolet A photograph. The flash units 40a, 40b, 50a, 50b, 20a, 20b, 30a, and 30b are triggered sequentially through the use of a radio transceiver (Pocket Wizard Multimax, LPA Design, South Burlington, Vt. USA) using transceivers 95 (attached to power pack 90 and operating in receiver mode), 96 (attached to power pack 91 and operating in receiver mode), 97 (attached to power pack 92 and operating in receiver mode), 98 (attached to power pack 93 and operating in receiver mode), and 99 (attached to the hot shoe of camera 11 and operating in transmitter mode). A Topas A2 power pack (Sinar Bron) is used for power packs 90 and 91 and a Primo 4 power pack (Sinar Bron) is used for power packs 92 and 93. The radio transceiver causes the activation of the pairs of flash units in response to the shutter release of camera 11.

Prior to taking the blue fluorescence photograph, the IDL software makes a call to servo motor 80, using a Mini SSC II circuit board (Scott Edwards Electronics, Sierra Vista, Ariz. USA), to move long pass filter 81 (Kodak Wratten No. 8, Eastman Kodak, Rochester, N.Y. USA) in front of the lens of camera 11. After this movement, the blue fluorescence photograph is taken. Following the taking of this photograph, the IDL software then makes another call to servo motor 80 to move long pass filter 81 away from the lens of camera 11. The IDL software then instructs the camera to take the remaining three images. Apparatus 100 is able to acquire these four images in about 10 seconds.

At this point, the four images just acquired are stored in the memory of camera 11 as separate data files. The IDL software then makes function calls to these data files and requests these files be transferred to the computer running the computer software and saved to its hard disk with a file name that indicates the apparatus used, subject identifier, and the type of image.

The subject is then presented on monitor 70 with a registration form. Examples of such questions include e-mail address, places where they buy skin-care products, ethnic background, and amount and type of skin-care products that they have purchased in the past (e.g., the past year).

The subject then begins reviewing each of the four images on monitor 70 and answers questions, presented on monitor 70, about each image. The computer program calls the IDL software and requests that a particular saved image be loaded from the hard disk and resized to fit in the screen display area. Once the image is displayed, the IDL software then returns control to the computer program. The facial image display area is roughly half of monitor 70. The other half of the screen of monitor 70 displays a series of questions relating to the particular displayed image. To assist the subject in the review of his/her images, the computer program may also display on monitor 70 images of other people as comparisons.

As the subject advances to the next page, the computer program calls IDL program and requests that a particular saved image be loaded from the hard disk and resized to fit in the screen of monitor 70 area as discussed above. This procedure continues until all four images have been displayed and all questions have been answered by the subject.

Upon viewing the standard photograph, the subject is then presented with questions regarding the surface of his/her skin. Examples of such questions include, but are not limited to, whether they have any fine lines, wrinkles, loss of elasticity or firmness, large visible pores, sensitive skin, and rough or smooth skin, as well as the severity and location of such conditions. Other questions include, but are not limited to, the frequency and severity of irritation from skin care products.

Upon viewing the polarized photograph, the subject is asked questions regarding the oiliness of their skin. Examples of such questions include, but are not limited to, whether they have normal, dry, oily, or selective oily skin (e.g., oil in certain areas such as above the eyebrows and on the tip of the nose).

Upon viewing the ultraviolet A photograph, the subject is asked questions regarding the visualization of pigmentation of the face (e.g., brown spots). Examples of such questions include, but are not limited to, the amount and location of such pigmented spots.

Upon viewing the blue fluorescence photograph, the subject is asked questions regarding acne. Examples of such questions include, but are not limited to, the severity and frequency of his/her breakouts.

As described above, the images from camera 11 are displayed on the computer monitor 70. However, because the number of available screen pixels are less than the number of actual image pixels taken by the digital photograph, only a small percentage of the original image can actually be displayed if the image is to be shown on the screen in its entirety while maintaining aspect ratio. For the case of the Nikon D1X, which stores 6 million pixels per image, display of the digital image in a portrait-orientation on a computer screen having a resolution of 1024×768 results in display of only 1 out of every 18 pixels. In such a down-sampled image presentation, fine detail of the skin taken by camera 11 is not fully displayed.

The solution to this problem is to use a technique whereby a 256×256 box (display kernel) appears directly over the area of interest and shows all the image pixels actually acquired by camera 11 for such area. The effect is an in-place magnification of a small area of the image on monitor 70. The apparent magnification, shown as this display kernel, can be passed over various areas of the image selected by the subject. Thus, this is an example of 1:1 image display (where every image pixel is shown on the screen within a small display kernel). True magnification of the image can also be accomplished by interpolating the data between pixels and creating additional pixels, thereby providing magnification of select areas of the image. The subject selects the magnification of such area by touching the area of interest displayed on the monitor 70.

Following the input of the answers from the subject, the computer program then proceeds to suggest skin care products for the subject. Each question in the computer program is associated with a skin condition. For example, the question "How often does your skin breakout?" is associated with acne. As the subject answers each question, the corresponding skin condition is assigned a degree. For example, the acne question has four degrees corresponding to the four answer choices: Always, Weekly, Monthly and Never.

After the subject answers all the questions, the skin conditions questioned by the computer program are ranked according to severity. This ranking is accomplished by passing all of the degree values entered by the subject to a relational database stored procedure contained within a relational database (Microsoft SQL, Microsoft Corporation, Redmond, Wash. USA) that is on the same computer.

A database table contained with the relational database contains a record for each skin problem type and degree. A "degree weight" is assigned to each record, which facilitates the ranking of the skin conditions. For example, if the subject answers "Always" for the above acne question, and "Yes" to the question "Do you notice any loss of firmness on your face?" the acne skin condition may have a higher rank than the loss of firmness condition. However, if the subject answers "Weekly" to the above acne question and "Yes" to the loss of firmness question, the loss of firmness condition may be ranked higher.

After the skin conditions are ranked, the top three conditions, along with the subject's skin type, e.g., normal, dry, or oily, are passed to another relational database stored procedure contained within the relational database. Using these values, this procedure queries a second database table that contains all of the possible combinations of skin conditions along with skin type. Each such record in the table contains a list of recommended products based on these values. This corresponding list of recommended products for that subject's condition is then passed back to the computer program.

Finally, the computer program creates a printout using Crystal Reports (Seagate Corporation, Scotts Valley, Calif. USA) for the subject including the suggested skin care products and pictures of the subject with information about the various skin conditions. At the conclusion of computer program, the subject will indicate whether or not the images should be kept or deleted.

Figure 2:
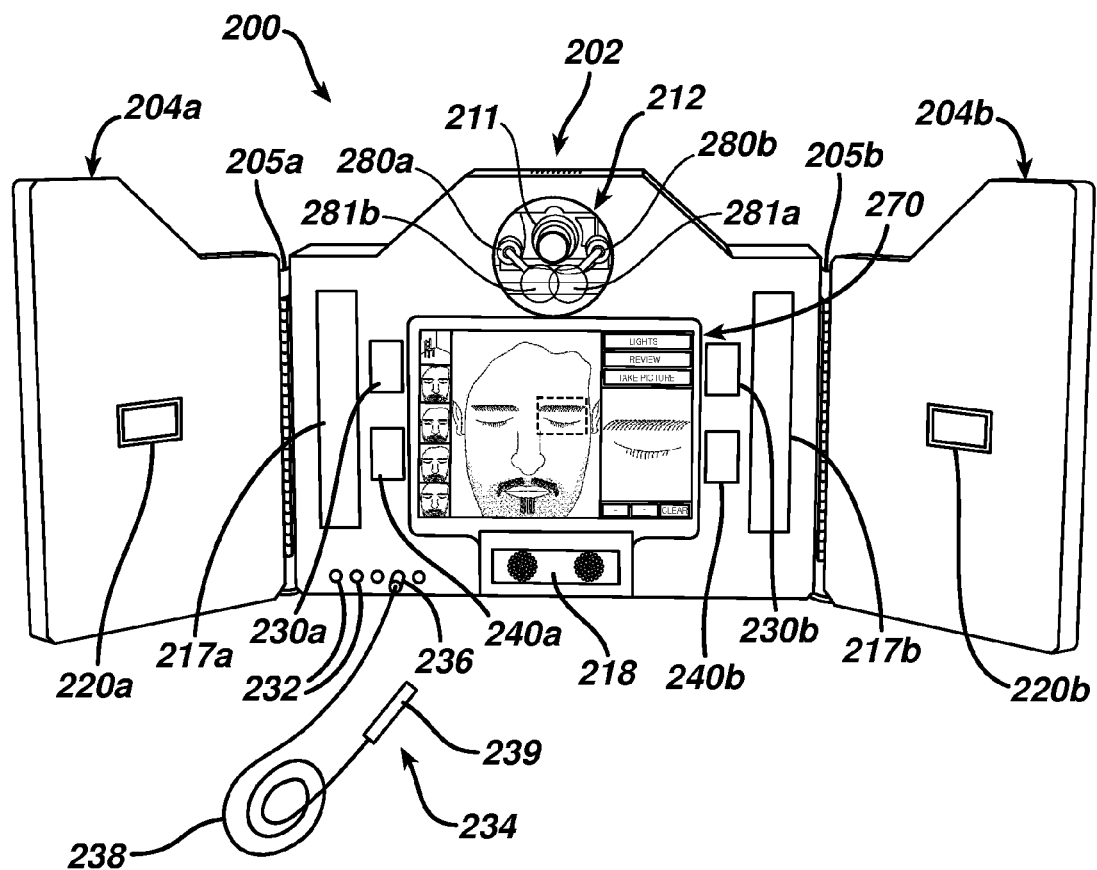
FIG. 2 is a perspective view of an alternative embodiment of the present invention.
Figure 3:
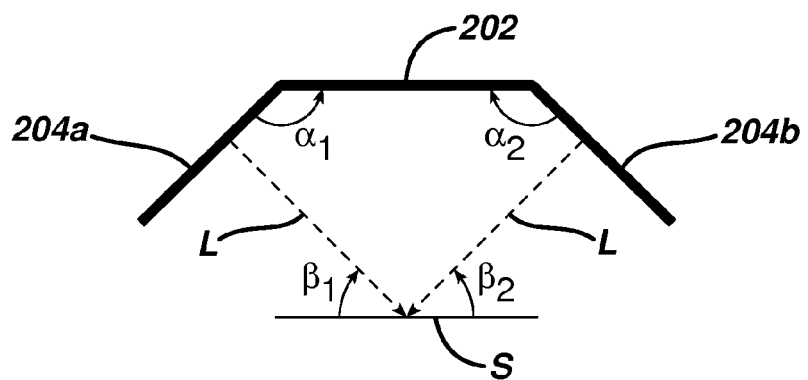
FIG. 3 is a diagrammatic top view of the present invention shown in FIG. 2, in particular, showing an angular orientation of a pair of doors thereof relative to a central housing thereof.

FIGS. 2 and 3 show an alternative embodiment of the present invention wherein imaging station 200 is provided in the form of a cabinet unit with a central housing 202 flanked by a pair of hingedly connected door assemblies 204a, 204b. The door assemblies 204a, 204b can be opened and closed relative to the central housing 202. FIG. 3 shows that the angle between the door assemblies 204a, 204b and the central housing 202 can be adjusted to adjust the angle of incident light cast on subjects by flash units mounted to the door assemblies 204a, 204b. The angular orientation α1, α2 of door assemblies 204a, 204b relative to the central housing 202 results in light L1, L2 emanating from flash units 220a, 220b, respectively, having an angle of incidence of β1 and β2, relative to the subject S. As noted above, the incidence angle of the light illuminating a subject S, can be selected to aid in capturing images which are more probative of skin condition, e.g., when capturing polarized light images.

The angles α1, α2 can be controlled by conventional means, such as an adjustable, threaded stop or a slotted, pivoting bracket coacting with a limit pin, as are commonly known for controlling the extent of opening of hingedly mounted doors and lids. In this manner an optimal angle for one or both door assemblies 204a, 204b is repeatable.

The embodiment of the present invention shown in FIG. 2 shares many features of the previously described kiosk embodiment and includes a camera 211 (preferably digital) placed within a camera niche 212 for capturing the images of a subject S. As noted above with respect to the kiosk embodiment, a number of different illuminating lights (flashes) are available for capturing images. More particularly, the imaging station 200 has fluorescent lights 217a, 217b, polarized flashes 220a, 220b, a pair of UVA flashes 230a, 230b having a wavelength of, e.g., 405 nanometers. A pair of UV flashes 240a, 240b having a wavelength, e.g., of 385 nanometers are positioned below the 405 nanometer flashes 230a, 230b. The flashes 230a, 230b and 220a, 220b may optionally be operated in conjunction with filters 281a, 281b that can be rotated in front of the camera lens by solenoids 280a, 280b to further select the wavelengths of light received by the camera 211. For example, a yellow filter 281a may be rotated in front of the camera 211 by solenoid 280b when taking pictures with the 405 nanometer flashes 230a, 230b. A polarizing filter 281b may be used in conjunction with polarized flashes 220a, 220b.

Various combinations of illuminating light(s) and filter(s) may be used for image capture. The present invention is not limited to the number and placement of flashes and filters shown. More particularly, a greater or lesser number of filters and flashes may be employed, e.g., see FIG. 9. While rotating filters 281a, 281b are described above, non-moving filters can be placed over one or more flashes to control the light wavelengths that are used to capture an image. Multiple standard flashes may be employed in conjunction with a variety of filters to achieve illumination under a variety of selected wavelengths of light. Combinations of flashes may be activated simultaneously to acquire a single image or sequentially to acquire multiple, sequential images. It should be noted that the use of multiple flashes with different filter options may be preferable under certain circumstances than utilizing a moveable filter. That is, by simplifying the imagining station 200 and reducing the number of moving parts, the imagining station 200, may be made more cheaply and function more reliably.

A touch screen monitor 270 is disposed below the camera 211 and displays the photographic images recently obtained by the camera 211 and/or previously obtained images that reside in memory or on a storage device, such as a computer disk or memory stick. A speaker 218 is provided in the imaging station 200 for announcing instructions to the user (subject S). The speaker 218 is particularly useful in giving instructions to the subjects when their eyes are closed, e.g., immediately prior to, during and immediately after a photographic session, when flashes are activated to capture images of the subject's face.

A plurality of sockets 232 are provided at the front of the imaging station 200 for receiving plug-in probes 234. Typically, the probes 234 will have a jack end 236, a cable portion 238 and a testing end 230. The testing end 230 would be held by a user in proximity to the area of skin to be tested. Alternatively, all probes 234 may remain connected and stored within the housing 202, e.g., with the cable 234 stored on a spring-wound reel and the probe held within a recessed well, accessible to the user who can withdraw it for use and allow it to retract when finished. As noted above, numerous probes suitable for analyzing various states and conditions of the skin are known. More particularly, an apparatus for conducting diffuse reflectance spectroscopy is described in the article, Non-Invasive Measurements of Skin Pigmentation in Situ, Stamatas, et al., Pigment Cell Res 17:618-126, 2004, which is incorporated by reference herein in its entirety. An apparatus and method for conducting fluorescence spectroscopy of the skin is described in Fluorescence Spectroscopy of the Skin, Kollias, et al., Vibrational Spectroscopy 28, 17-23, (2002), which is incorporated by reference herein in its entirety. Probes for measuring the elasticity of the skin (Reviscometer®) and probes for measuring skin surface hydration (Corneometer®) can be obtained from Courage & Khazaka Electronic GmbH, Koln, Germany. The conductivity of the skin can be measured by a NovaMeter® or Nova Petite® sold by Nova Technology Corporation of Portsmouth, N.H. or the SkiCon hygrometer by IBS, Inc. of Hamamatsu, Japan.

Figure 4:
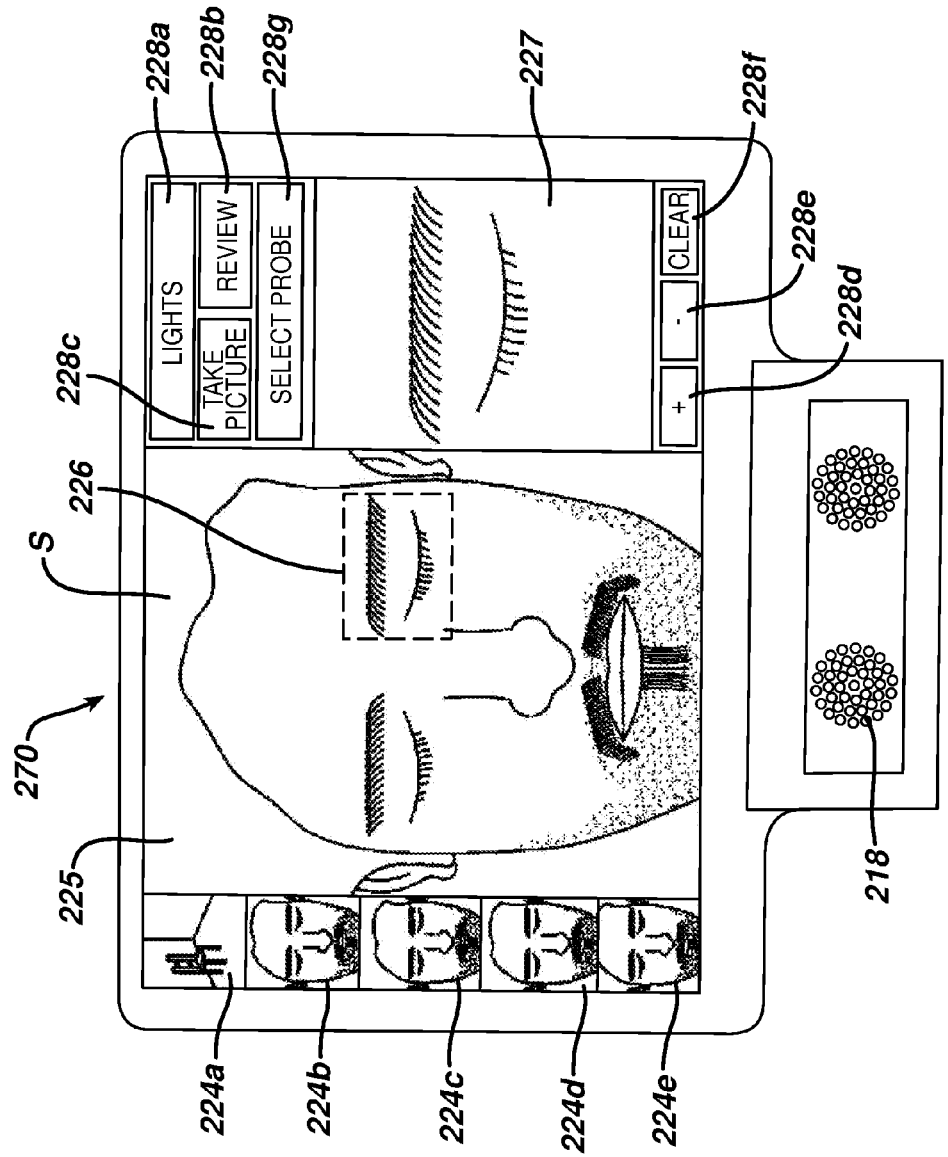
FIG. 4 is an elevational view of a touch screen display of the present invention shown in FIG. 2.

FIG. 4 shows an enlarged view of the monitor 270 which is preferably a touch screen monitor allowing the simultaneous display of information and the processing of control inputs from the operator/user/subject S who touches the screen to select control options. In this manner, the operator may control the images displayed to review and study them for the purposes of diagnosing and evaluating skin condition. At the left side of the display monitor 270 a plurality of thumbnail images 224a through 224e may be displayed. The first thumbnail image 224a may be utilized to display (both in thumbnail and in enlarged format) a real time moving image captured by the camera 211 in video mode which permits the user to interactively view and position their face in front of the camera for centering and focusing and optimally capturing their facial image. The real time image is therefore, in some respects, like a mirror. To initiate an imaging session, a computer program may be used to inform the user, either through visually displayed instructions or auditory instructions, to position their face such that it substantially fills the display frame and is centered therein.

The remaining thumbnail images 224b through 224e may be used to display images that have been captured during an imaging session utilizing different wavelengths of illuminating light. As described above with respect to the kiosk embodiment, the imaging station 200 preferably takes a sequence of images utilizing different wavelengths of light, via different flashes and filters, etc. in order to capture images which reveal different attributes of the subject's skin. Selecting one of the thumbnail images 224b through 224e by touching it will cause that particular image to be displayed in the main display area 225 on a larger scale Optionally, the thumbnail images 224a-224e may be labeled with text indicating the type of image that it is, e.g., "Blue Light" or "White Light" and/or the time and date when taken. Selecting a thumbnail image of a particular type may invoke instructions and observations from the computer in the imaging station 200 which relate to that particular type of image. For example, the computer program may announce a particular type of image has been selected and provide tips on what is shown by this type of image—"You have selected a blue light image. This type of image is particularly useful in assessing condition(s) X, Y, Z. In making this assessment, look for A, B, C in the image, which are indicative of D, E, F . . . " This type of message can be delivered in text on the display and/or in audio form over speaker 218. The delivery of this type of message is preferably enabled/disabled under operator control, e.g., by touching a control button, "Enable/Disable Instructional Messaging" or an equivalent control means. The foregoing highlights that in order to effectively employ the imaging station 200, the observer of the captured image is preferably educated in the technique of observing and interpreting features apparent in the captured images. The pertinent information for effectively using the imaging station 200 may be communicated to the user/subject S by the above-noted messaging, but also by written and/or recorded materials provided with the station 200 (e.g. in CD ROM or video form). In the event that the imaging station is connected to the Internet, information can be provided to the user/subject S interactively by retrieving the information from a website and presenting it to the user/subject S at appropriate times or by presenting hyper links that the user/subject may activate based upon interest. By surveying the main image area 225, the user can ascertain the presence or absence of certain skin conditions revealed by the particular light that was used in capturing the image. The thumbnail images therefore provide an intuitive and transparent means for identifying and reviewing a plurality of images taken during an imaging session. While the imaging method described above suggests that multiple images are captured by multiple sequential exposures of a static subject S with different wavelengths of light, the present invention may also be utilized to take one or more pictures after the subject S had varied their position. For example, a series of polarized images may be captured with the subject being instructed to rotate their face from left silhouette, to a forward facing position, to a right silhouette position, or in varying degrees of looking up, down and straight ahead. While the present invention is very useful for examining the face, images of other surfaces of the body may also be captured, recorded and analyzed. For example, the status and progress of a burn, abrasion, rash, melanoma, mole or other skin condition on any part of the body may be observed and analyzed using the present invention.

On the upper right hand portion of the display monitor 270, a plurality of virtual control buttons 228a-228c are displayed and in the lower right hand portion, control buttons 228d-228g are displayed. Control button 228a controls the fluorescent lighting 217a, 217b (on/off and/or dim down/brighten), which illuminates the subject S in a darkened room and allows the subject S to position his or her face before the camera (as shown in thumbnail 224a). (In order to control the wavelengths of light in which images are taken, it is preferable to have reduced ambient illumination, e.g., due to room lighting). Control button 228b is utilized to review old images taken at a prior photo session. By reviewing images taken at different times, a user can compare the progress of their skin condition over time. Preferably, the imaging station 200 permits the selection of a plurality of images to be displayed, e.g., two or three, in large scale, juxtaposed next to one another. This permits side-by-side comparison to observe trends in skin condition over time or to compare images taken under different lighting conditions, e.g., comparing a polarized light image to a white light image. Control button 228c may be used to initiate a photo session after the user has positioned themselves properly before the camera 211. A prompt may be provided instructing the user/subject S to press control button 228c after they have positioned themselves.

An enlarged (magnified kernel) display area 227 displays a portion of the main image area 225 at a greater level of magnification. The portion that is magnified is determined by focus box 226, which is overlaid on the image displayed in the main display area 225. The purpose of the enlarged display area 227 is to focus upon a specific area of the image shown in the main display area 225 for closer examination, at a greater magnification. Accordingly, the user may position the focus box 226 over any area of the image shown in display area 225 by touching the monitor/screen 270 in the area delimited by the focus box 226 and "dragging" the focus box 226 to the area of interest on the image in the main display area 225. The corresponding portion of the image bounded by the focus box 226 is then displayed in the enlarged display area 227. The image portion shown in enlarged display area 227 may then be further enlarged or reduced (zoom in and out) by the control buttons 228d and 228e ("+" indicating zoom in for greater magnification and "−" indicating zoom out for lesser magnification). The enlarged display area 227 may also be cleared by touching control button 228f.

As noted above, the comparison of side-by-side images may at times be instructive. This comparative process using, e.g., a pair of side-by-side images of a person's face taken under the same lighting conditions but at different times or at the same time but using different lighting, can be further enhanced by performing zooming and focusing functions on one or both images. One embodiment involves coordinated or synchronized focusing and zooming. More particularly, when viewing a pair of images, the focus box graphic appearing in each of the images may be located on the same place in each image (e.g., on the tip of the nose). When the focus box is moved on one of the images, an equal displacement of the focus box on the other image is effected. For example, if the focus box on both of the images is on the tip of the nose and the user/subject S moves the focus box on one of the images to the eye area, then the focus box on the other image moves to the eye area also. Zooming can also be coordinated in the same manner, such that when comparing side-by-side images, the focus area and magnification are the same, promoting comparison.

Button 228g may be used to select a probe for examination/analysis of the skin using a probe as described above. A menu of available probes along with a description of the function of each would be displayed to aid the user in selecting a particular probe. Following selection, the user would be given instructions on use on-screen and/or over the speaker 18, as described more fully below.

Figure 5:
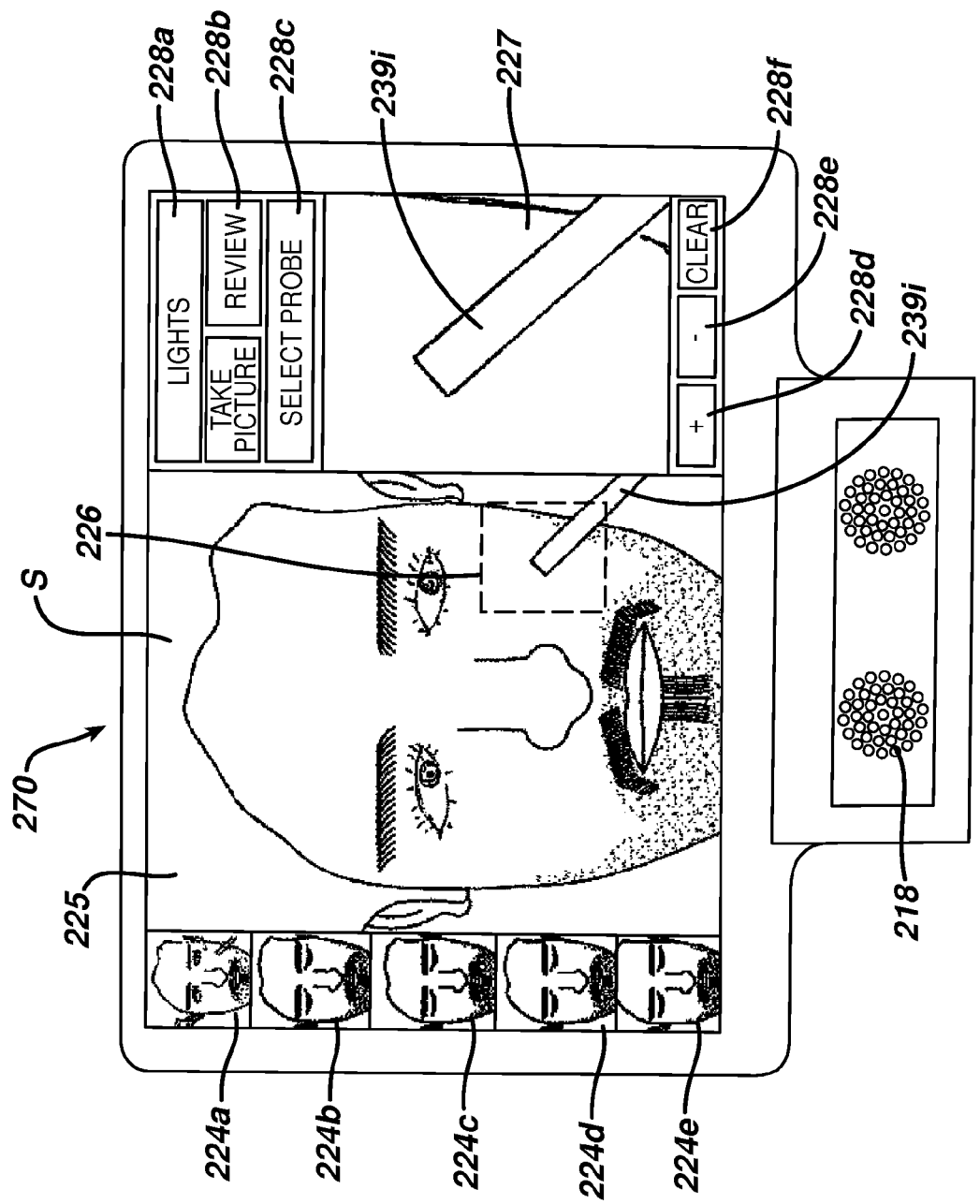
FIG. 5 is an elevational view of the touch screen of FIG. 4 in another mode of operation.

FIG. 5 shows an exemplary state of the monitor 270 as it would appear after selection of a specific probe 234, with the subject S interactively positioning the probe over the area of interest. One of the benefits of the present invention is that it provides a means for focused analysis of a particular area of the skin surface, i.e., by means of a probe 234. More particularly, the imaging capability of the imaging station 200 may indicate a particular area of the skin which exhibits a condition of concern or interest, e.g., an area of redness, irritation, pigmentation, etc. This area of interest can then be examined by positioning the probe over it and activating the probe to initiate testing and recording of the test results. The imaging station 200 facilitates this process, e.g., by allowing the user to select the live video thumbnail which then causes the subject S to appear on the main display area 225 in real time. In addition, the enlarged display area 227 defined by the focus box 226 displays the area of interest on the skin in a magnified image to aid the Subject to place the probe in the correct position for testing. One benefit of conducting spot checks in this manner is to isolate data for areas that are pertinent while ignoring other areas that do not need to be considered. Another benefit realized by the invention, is that the probe data may be quantified and stored. Quantification of skin condition is useful for conducting objective evaluations and also to monitor a skin condition more precisely based upon the comparison of quantified results taken from two or more tests conducted at different times. For example, if an area of irritation is tested to ascertain skin conductivity or redness weekly over the course of 4 weeks, during which a course of therapy is used, a comparison of the quantified results (numerically or graphically) can more readily indicate the trend of the skin condition, than a subjective evaluation by the subject S or another person based upon their recollection of the prior states of the area of interest.

Figure 6:
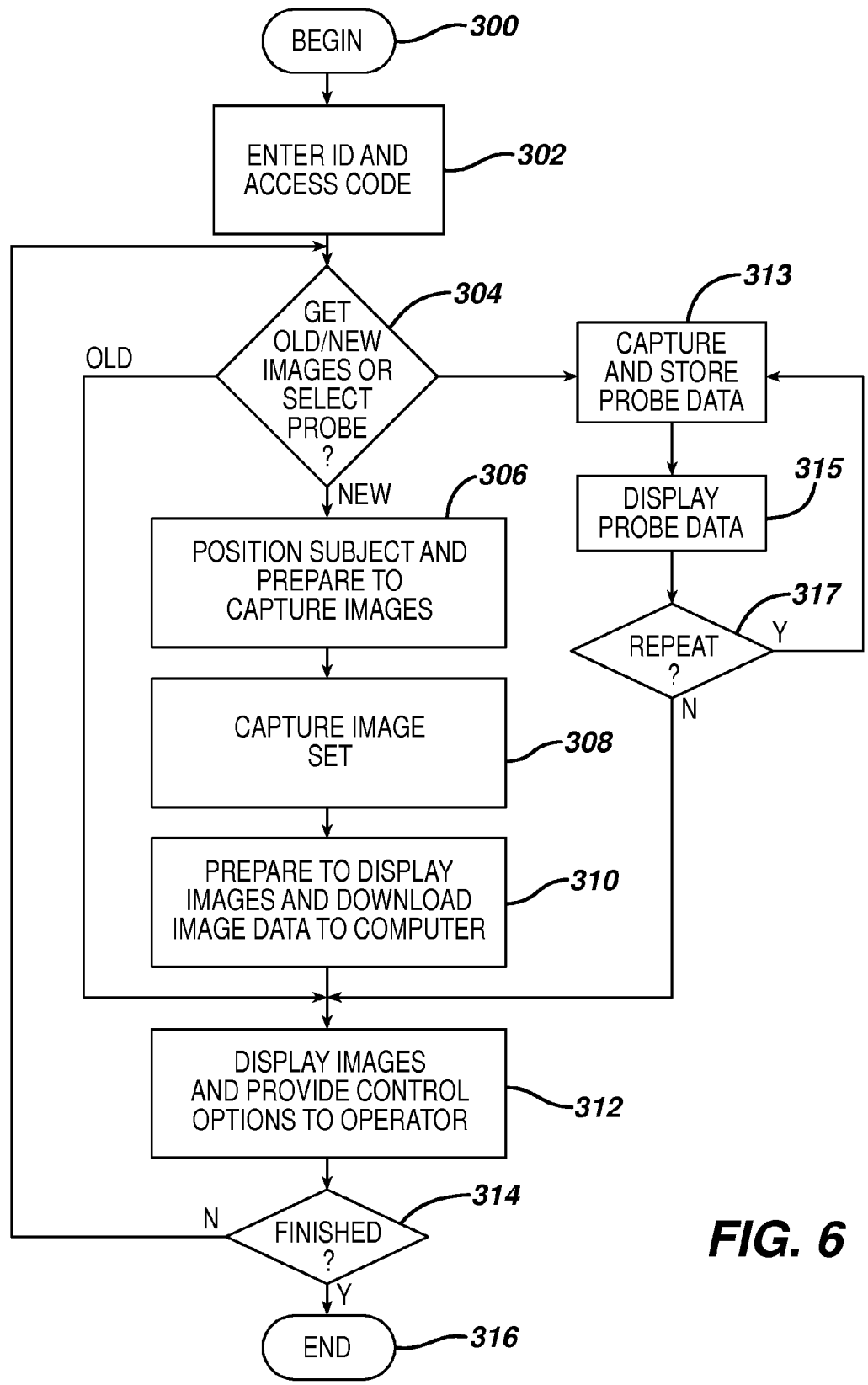
FIGS. 6 through 10 are flow charts showing exemplary processing flows associated with the operation and control of the present invention shown in FIGS. 2 through 5.

FIG. 6 shows exemplary processing steps that an exemplary embodiment of the present invention would utilize in obtaining and viewing the images of a subject S. The processing flow begins 300 by the operator entering an access code or an I.D. password 302. This is an optional step in the event that the imaging station 200 is utilized by more than one person. For example, if the imaging station were a public facility, the individuals who utilize it would prefer that their images would remain private and accessible only by them upon entry of a suitable password/access code. In the event that the imaging station 200 is a private facility, for example, located in the home of the user, then it would not be necessary for a password to be utilized.

At the beginning of the session, it is determined 304 whether the purpose of the session is to get new images, to review old images or to select a probe. This can be implemented by simply sensing on the control buttons 228b, 228c and 228g which provide the user with these options. If the user elects to take new images, for example, by touching control button 228c, the imaging station 200 provides instructions to the subject S to position themselves and to prepare to capture the images 306. For example, the subject may be instructed to approach the camera such that their face fills the field of view as shown in thumbnail 224a. Once positioned, the subject is instructed to turn off the fluorescent lights and/or to close their eyes to prevent the flashes from being seen. Once the subject S indicates a ready state, e.g., by pressing a button, e.g., 228c for taking pictures or by the system sensing that the subject S has turned off the fluorescent lights, the image set can be captured 308 by sequentially taking pictures utilizing different flashes and filters. The images are then prepared to be displayed and downloaded 310 to the computer of the imaging station 200. Once the images have been captured and downloaded onto the system computer, the images may be displayed 312 on the monitor 270 and the operator is provided with various control options. When the operator is finished 314 reviewing the images, the operation is at an end 316, otherwise, the user may obtain additional new images or review old images.

In the event that the user elects to select a probe by pressing button 228c, then the procedures necessary to capture and store the probe data 313 and display the probe data 315 are initiated. The user may then be given the option of repeating the probe test such that a sequence of test results are obtained. The camera may take a picture at the same time the probe test is conducted in order to create a correlation between the test result data and the position of the probe, i.e., by momentarily changing the mode of the camera from video mode to camera mode, taking the picture and then returning to video mode.

Figure 7:
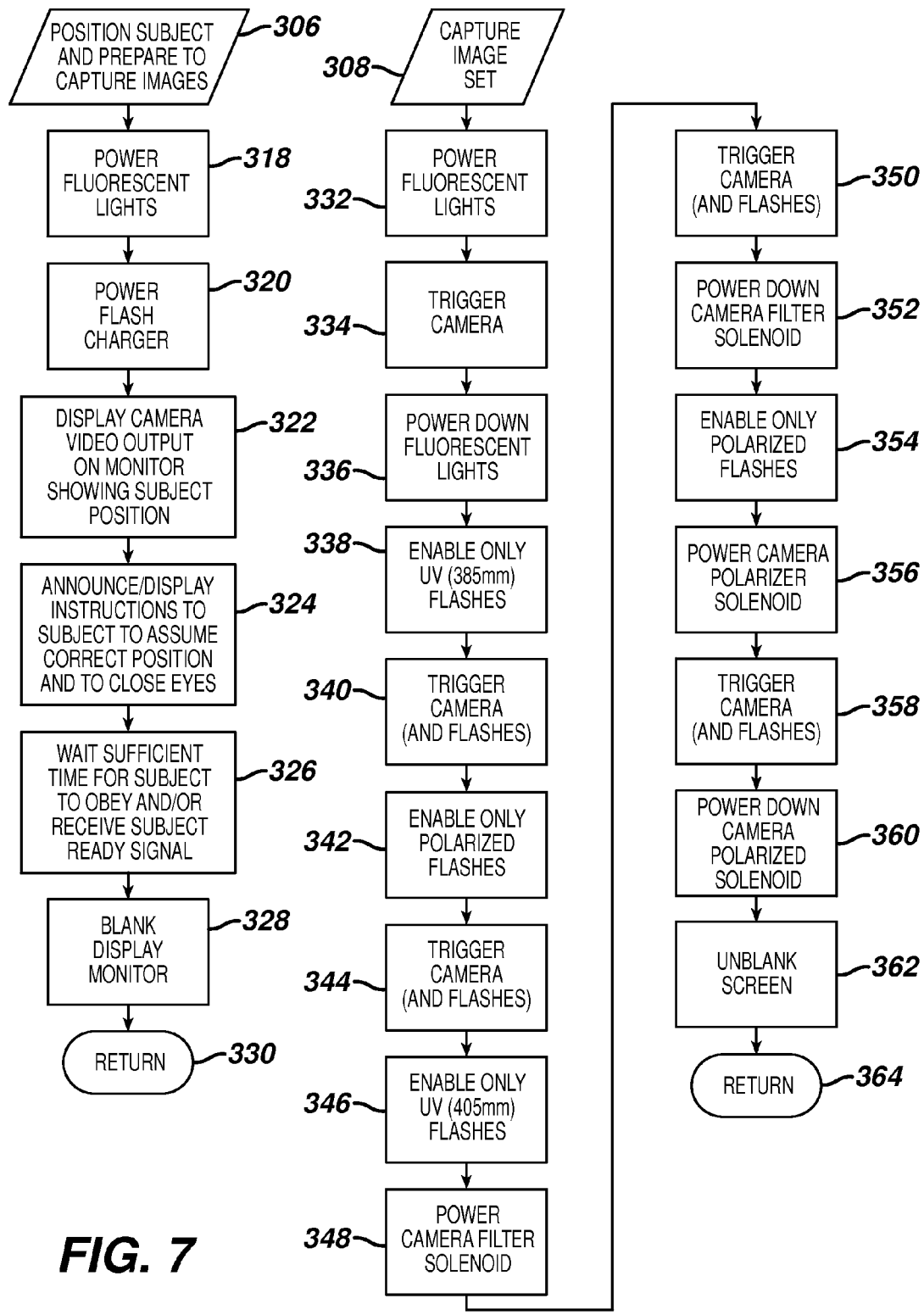
Figure 8:
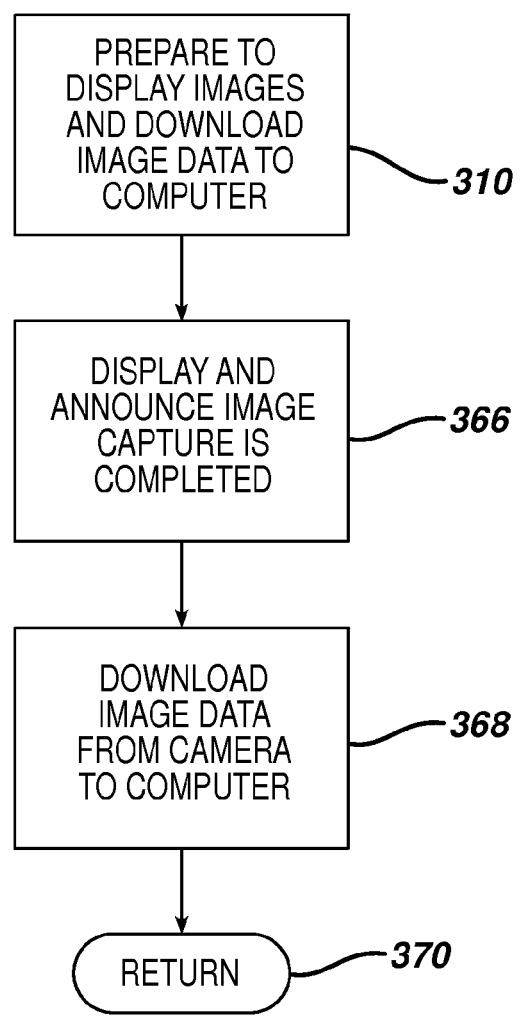

FIGS. 7 and 8 show the basic process shown in FIG. 6, in greater detail, namely, the step of positioning and preparing 306 to capture images includes powering 318 the fluorescent lights, powering 320 the flash charger and displaying 322 the camera video output on the monitor 270 so that the subject S may ascertain their position relative to the camera 322. As described above, this image is shown in thumbnail 224a or elsewhere as determined by the programmer. The program announces and/or displays 324 instructions to the user/subject to place themselves at the correct position relative to the camera and to close their eyes. A delay is provided 326, to give the subject S sufficient time to obey the commands for positioning and closing of the eyes and/or the computer program enables 326 a subject-ready signal, such as the subject pressing control button 228C to initiate taking pictures. The display monitor 270 is blanked 328 to avoid interfering with the illuminating light, and a return of control 330 to the main processing flow is executed. In capturing 308, the image set, the fluorescent lights 217a, 217b are powered 332 and the camera 211 is triggered 334. The fluorescent lights 217a, 217b are then powered down 336 and the 385 nanometer UV flashes 240a, 240b are enabled 338. The camera is then triggered 340 causing the 385 nanometer UV flashes 240a, 240b to flash. The polarized flashes 220a, 220b are enabled 342 and the camera 211 is triggered, triggering 344 the polarized flashes 220a, 22b. The 405 nanometer flashes 230a, 230b are enabled 346 and the camera filter solenoid 280b is powered 348, thereby moving the filter 281a in front of the camera 211. The camera 211 is then triggered 350 along with the flashes 230a, 230b. The filter 281a is then removed from a position in front of the camera 211 by powering down 352 the filter solenoid 280b. The polarized flashes 220a, 220b are enabled 354 and the camera polarizer solenoid 280a is powered 356 thereby moving the polarizing filter 281b in front of the camera 211. The camera 211 is then triggered, flashing 358 the polarized flashes 220a, 220b. The camera polarizer solenoid 280a is powered down 360 to remove the polarizing filter 281b away from the front of the camera 211. The display screen 270 is unblanked 362 and control returns 364 to the main processing flow.

To prepare to display images and download 310 the image data to the computer 552 (FIG. 9), the computer program announces 366 that the image capture is complete and then the image data is downloaded 368 from the camera 211 to the computer 552, where it is stored in memory or on a memory storage device. Control returns 370 to the main processing flow.

Figure 9:
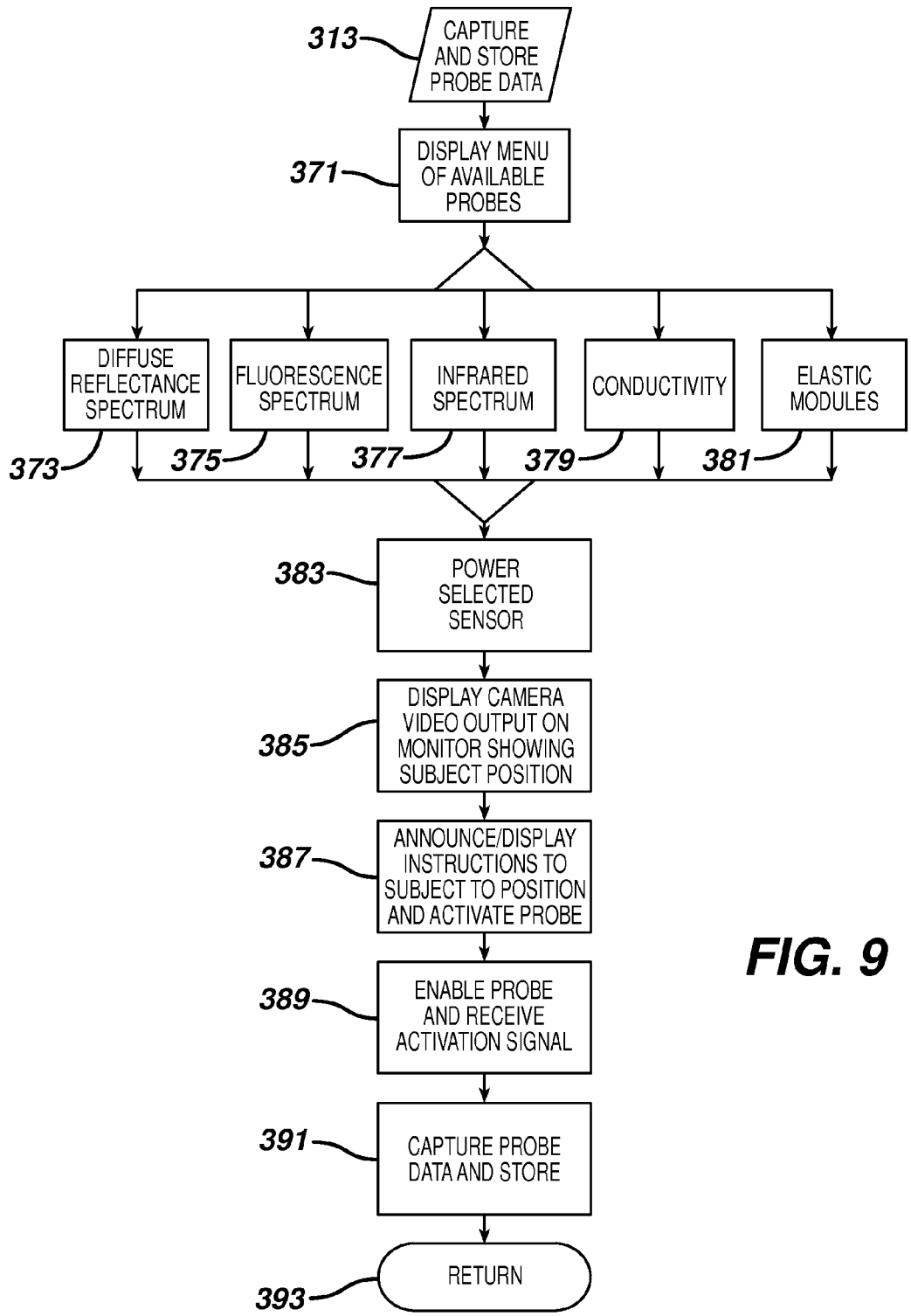

FIG. 9 shows exemplary processing steps associated with capturing and storing probe data 313. A menu of available probes is displayed 371, including a diffuse reflectance spectrum 373, fluorescent spectrum 375, infrared spectrum 377, conductivity 379 and elastic modulus 381. Other probes that are known in the art for measuring and testing skin condition could readily be employed and would fall within the scope of the present invention. Power is then applied to the selected probe/sensor 383. The camera is placed in video mode and the image is displayed in the main display area as well as the enlarged image area 385. Instructions for use of the particular probe selected are then either displayed and/or announced over the speaker. These instructions would cover the positioning of the probe on the person and how to enable/activate the probe for taking testing in the area on which it is applied. After the probe has been powered and reached a ready-for-testing state, the subject has been instructed on use of the probe and has indicated a readiness for testing by touching a button on the monitor or depressing a control button on the probe, the probe is enabled 389 and the activation signal is received triggering the probe into testing. The test data is then captured and stored to the computer memory 391. Control then returns 393 to the user via the touch screen display.

Figure 10:
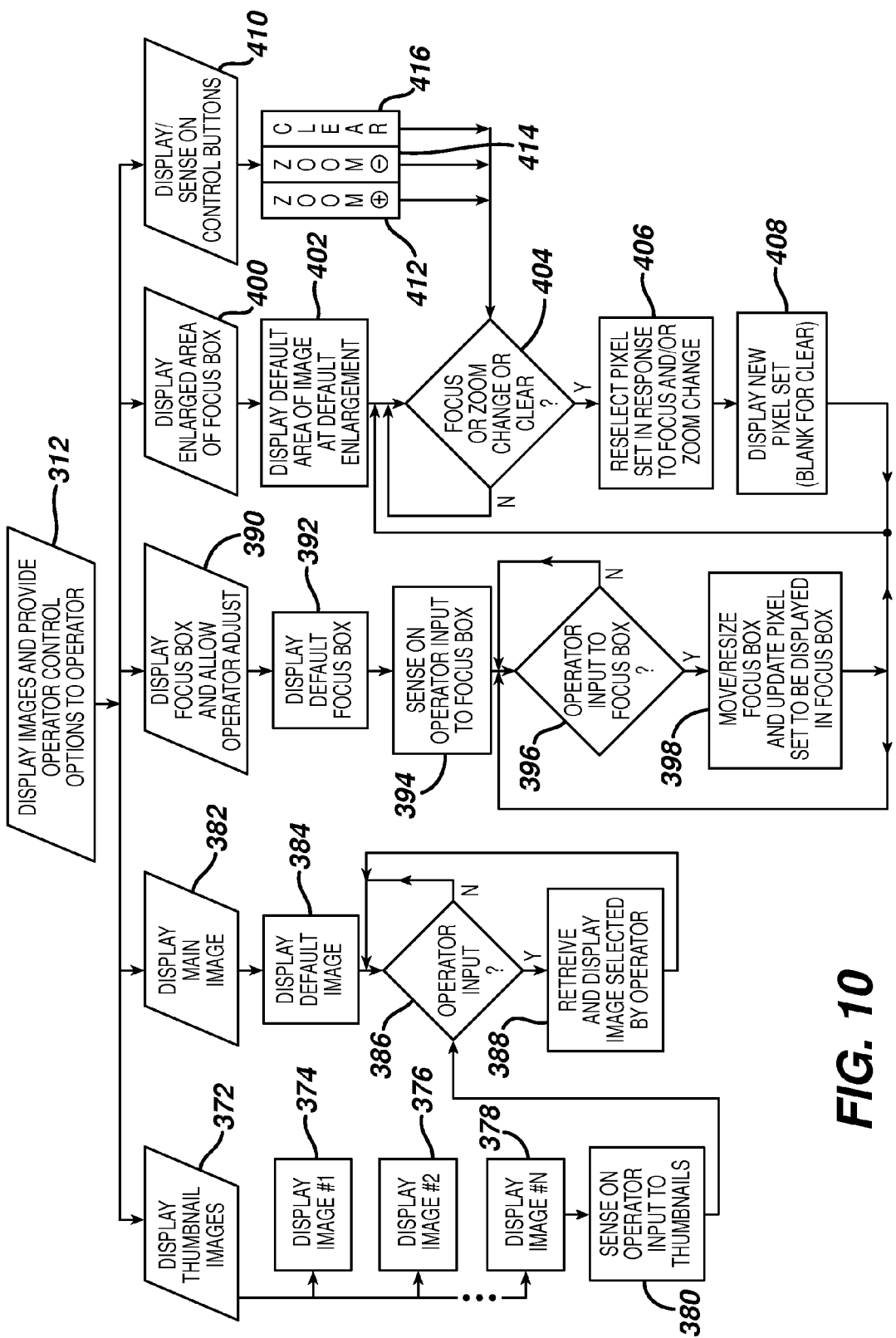

FIG. 10 shows exemplary processing associated with displaying 312 images and providing operator control options to the operator/subject S. As noted above, the display 270 has a plurality of thumbnail images 224a through 224e. Any number of thumbnail images may be displayed 372 as indicated by the dotted lines and reference to display 374 image #1, display 376 image #2 and display 378 image #n. Because the display monitor 270 is preferably a touch screen monitor, the thumbnail display areas 224a through 224e can be used to sense on 380 operator input (touching the particular thumbnail image 224a-224b that the operator wishes to display in the main display area 225). In displaying 382 the main image, a default image is displayed 384 which would typically be the first image taken, e.g., an image taken in white light or fluorescent light. Based upon the operator input 386 (touching a particular thumbnail image), the image associated with that particular thumbnail 224b through 224e is retrieved 388 from memory or from a storage device and the image is displayed in the main image area 225. As noted above, a focus box 226 is displayed 390 in the main image area 225. A default focus box 226 is displayed 392 first and then the program senses 394 upon operator input to the focus box 226 for changes. More particularly, if the operator/subject S touches the display screen 270 within the boundaries of the focus box 226 and retains contact with it while moving the contacting finger across the screen 270, the focus box 226 can be dragged to the area of the image of interest to the operator/subject S. Operator inputs to the focus box location are monitored at step 396. If there has been a change, then the pixel set associated with the focus box 226 is updated 398. The magnified image associated with the focus box 226 is displayed 400 and a default area associated with a default position of the focus box 226 is displayed 402 first. The program continually senses 404 upon changes in focus or zoom or for "clear" signals that are generated by the operator touching one of the control buttons 228d, 228e, 228f. Any of these inputs causes the pixel set associated with the focus box to be reselected 406 and displayed 408 in order to implement a focus or zoom change and/or for clearing the display. At Step 410, the control buttons "+", "−" and "clear" are displayed and sensed upon. As noted above, touching 412 "+" results in enlargement of the image displayed in the enlarged display area 227. Pressing 414 "−" results in a lower magnification and pressing 416 "clear" results in the enlarged display area 227 being blanked. In addition, add control buttons, e.g., 228a-228g are displayed and sensed or to invoke the various processing choices described above.

Figure 11:
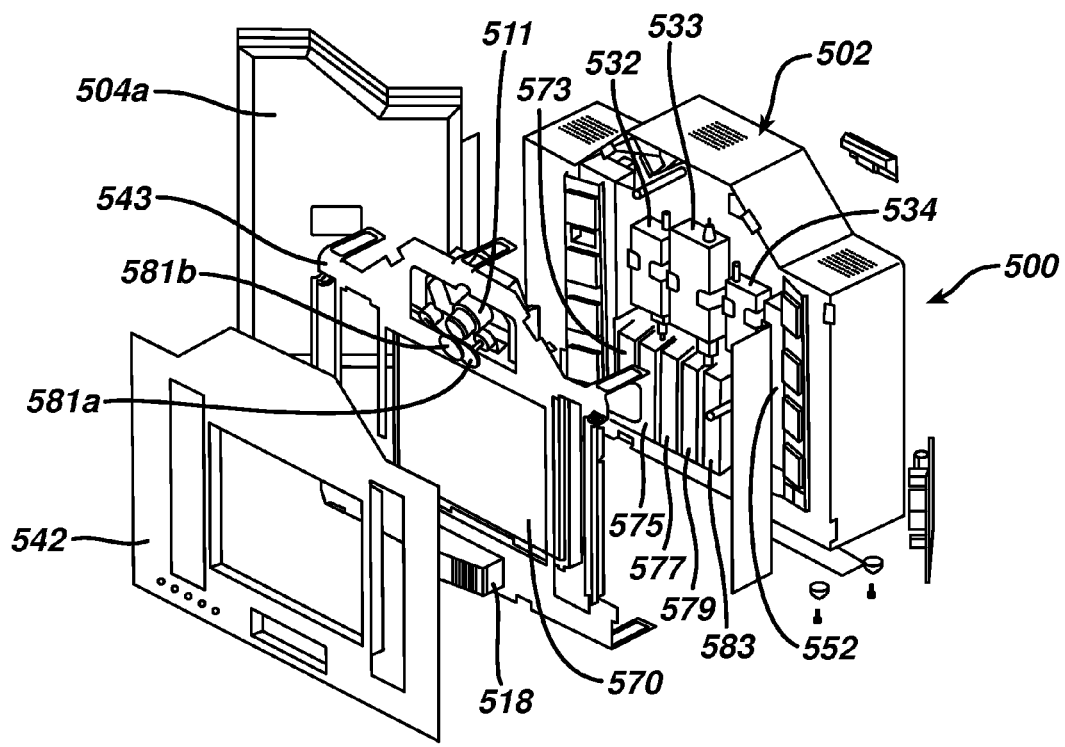
FIG. 11 is an exploded view of the present invention as shown in FIGS. 2 through 5.

FIG. 11 shows an exploded view of an embodiment of the present invention in which, imaging station 500 has center housing 502 containing a plurality of power supplies 532, 533, 534 for powering the various system elements, including the monitor 570 and the system computer 552, as well as the camera 511. The camera 511 is mounted on an intermediate panel 543 which also serves to provide a structure for mounting the monitor 570. The intermediate panel 543 is received in and attached to the housing 502 by conventional fasteners, such as threaded fasteners or rivets. Front panel 542 is attached to the housing 502 and/or intermediate panel 543. The front panel 542 has apertures for camera 511, speaker 518 and monitor 570. Only one door assembly 504a is shown. Either single or plural door configurations are within the scope of the present invention, as are configurations where the door(s) open up or down.

The spectrometers and other apparatus 573, 575, 577, 579 and 583 supporting the probes 234 for conducting testing and sampling based upon the diffuse reflectance spectrum, fluorescent spectrum, infrared spectrum, conductivity, and elastic modulus, respectively, are contained in the housing 502.

Figure 12:
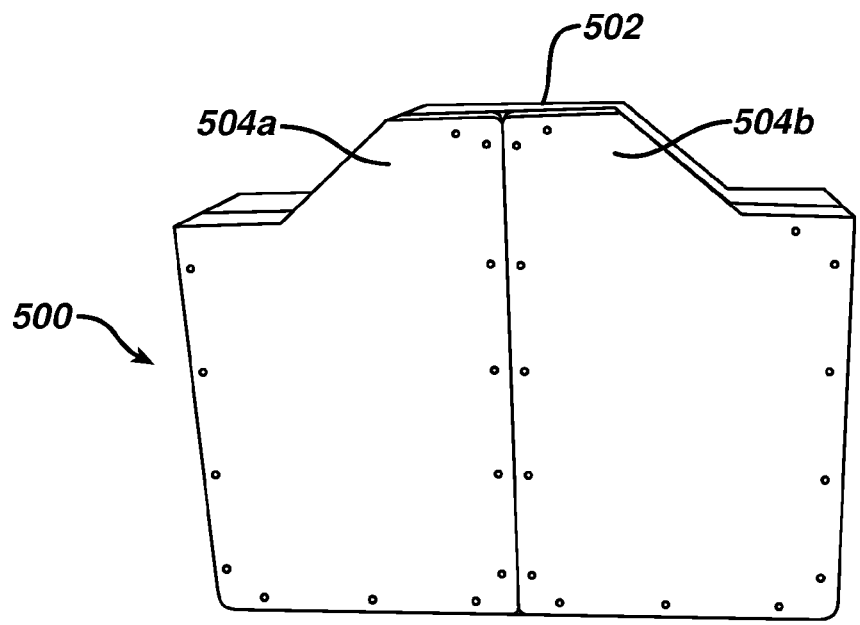
FIG. 12 is a perspective view of the present invention shown in FIGS. 2 through 5 and 11 with the doors closed.

FIG. 12 shows the imaging station 500 of FIG. 9 in a closed condition with door panels 504a and 504b closed, such that the monitor 570 is not visible. This embodiment of the imaging station 500 has some similarities to a conventional medicine cabinet in that it can be mounted on a wall and the doors 504a, 504b closed to protect the interior contents of the housing 502. The front surfaces of the door assemblies 504a, 504b may be mirrored.

Figure 13:
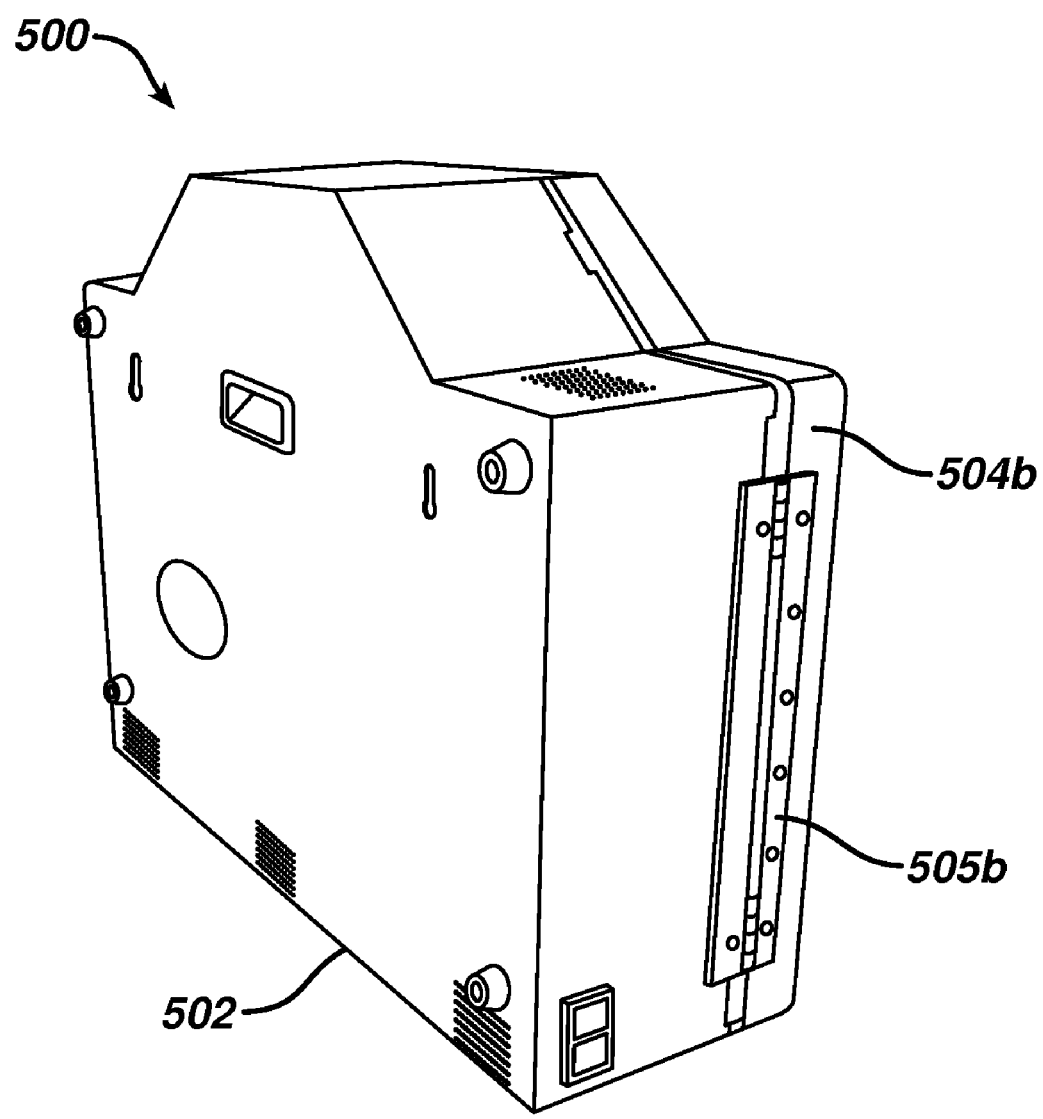
FIG. 13 is a perspective view of the present invention shown in FIG. 12, viewed from the rear.

FIG. 13 is a rear view of the imaging station 500 illustrating that the door assemblies 504a, 504b are hingedly attached to the housing 502 by hinges e.g., 505b.

Figure 14:
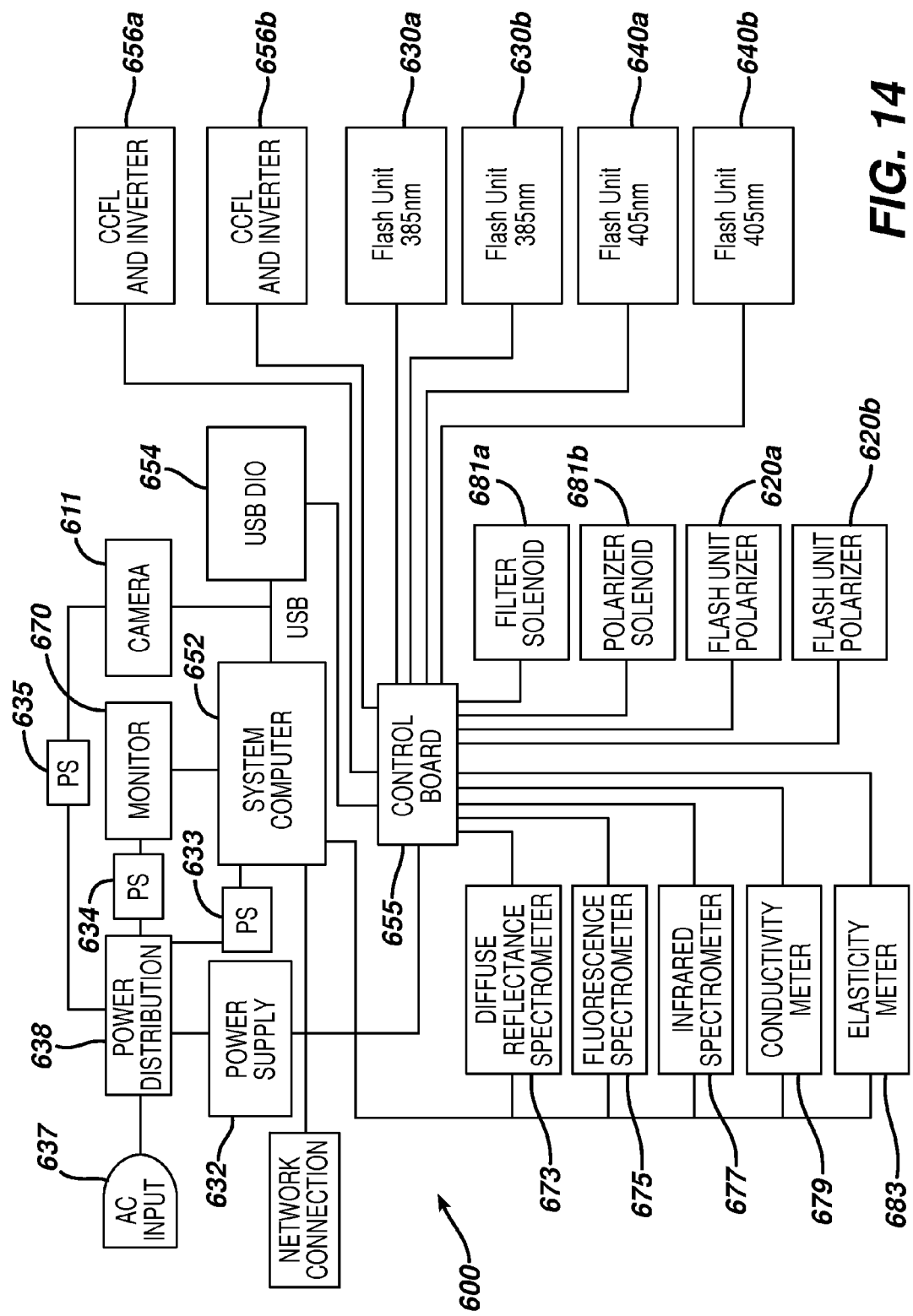
FIG. 14 is a block diagram showing the system components of the present invention shown in FIGS. 2 through 13.

FIG. 14 is a block diagram illustrating the electrical components of the imaging station 600. As can be appreciated, AC input 637 is routed to a power distribution box 638 for spreading the AC input to a plurality of power supplies 632, 633, 634, 635, which power control board 655, computer 652, monitor 670 and camera 611, respectively. Camera 611 communicates with the computer 652 via a U.S.B. data input/output 654 and thereby to transfer images to the control board 655. The control board 655 controls filter solenoids 681a, 681b, flash unit polarizers 620a, 620b, CCFLs and inverters 656a, 656b and flash units 630a, 630b, 640a and 640b, as well as, diffuse reflectance spectrometer 673, fluorescence spectrometer 675, infrared spectrometer 677, conductivity meter 679 and elasticity meter 683. Output from the various probe units 673-683 are sent to system computer 652 for storage and/or analysis.

While the present invention has been explained above in terms of an apparatus and method employing multiple images captured under different lighting conditions e.g., different wavelengths of light, the present invention would still be applicable to the capture and analysis of even a single image taken under selected lighting conditions. For example, the imaging station 200 could be utilized to capture and analyze a single image taken with blue light.

It should be appreciated that the present invention 200 is intended to be operated by any person and therefore can be utilized in a private setting, such as the home, by the subject S.

Figure 15:
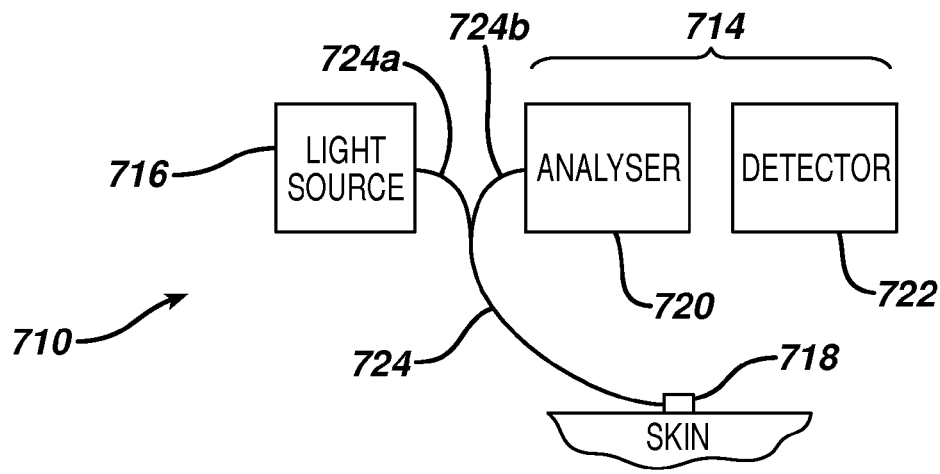
FIG. 15 is a diagram of a spectrometer for performing diffuse reflectance spectroscopy.

FIG. 15 shows a spectrometer apparatus 710 for performing diffuse reflectance spectroscopy (DRS) on skin. In DRS, light is delivered onto the skin and the resultant remitted light is collected and analyzed with a spectrometer 714. Many manufacturers provide portable spectrometers, e.g., Ocean-Optics (Boca Raton, Fla., USA), Newport (Irvine, Calif., USA), B&W Tek (Newark, Del., USA), CDI (South Bend, Ind., USA) and Minolta (Ramsey, N.J., USA). The components that are required for a DRS system are a light source 716, a probe 718, an analyzer 720, and a detector 722. A variety of light sources 716 have been used, such as tungsten halogen lamps, xenon arc lamps, broad-band white LEDs, etc. The choice depends on the wavelength range of interest.

Figure 16:
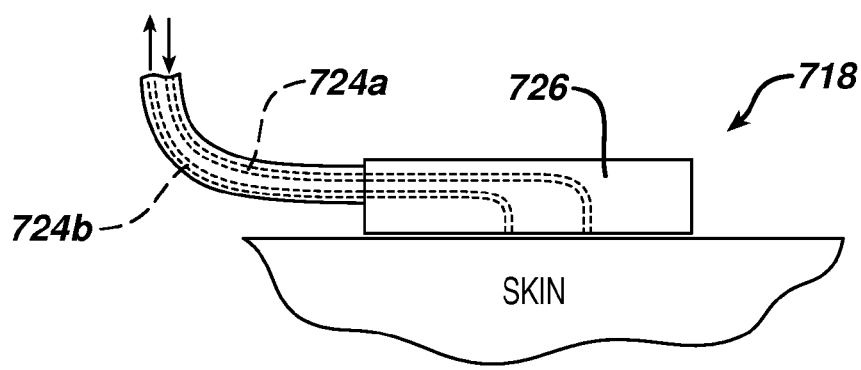
FIG. 16 is a diagram of a spectrometer probe for the spectrometer of FIG. 15.

The illumination light can be delivered to the skin site of interest through a bifurcated fiber optic bundle 724. Several designs have been used in the literature including randomly mixed fibers or particular geometries for illumination and collection. The fiber geometry is important as the fiber size and distance between illumination and collection fibers affect the sampling volume and the sampling depth. For example, if the illumination and collection fibers are adjacent one another, a fiber diameter of about 50 µm will result in a high sampling volume of light collected from a depth of about 80-120 µm. Smaller diameter fibers correspond to light collection from shallower depths below the skin surface. As shown in FIG. 16, it is useful to have a probe 718 with the fibers 724a, 724b bent to 90° at the common terminal 726 of the bundle 724 that comes in contact with the skin. This facilitates the use of the probe 718 with minimal pressure to the skin so that capillary constriction and skin blanching are avoided. Another way of collecting spectra is through an integrating sphere, which allows the collection of remitted light from all possible angles, but has the disadvantage that the probe size is limited by the aperture of the sphere. Probe size limitations prohibit the use of integrating spheres in cases where small skin areas are measured (e.g., small lesions). Note that the illuminated spot needs to be smaller than the integrating sphere aperture to allow for collection of light scattered deeper in the tissue (in particular for the long wavelengths that propagate further). The analyzer-detector system 714 can be in the form of a circular variable wavelength interference filter coupled to a silicon photodiode (32) or a diffraction grating coupled to a detector array, e.g., a linear charge-couple device (CCD) array or a photodiode array. The latter has the advantage of simultaneous acquisition of the whole spectrum.

Typically, prior to measurements, the detector dark current D is recorded and a spectrum is acquired from a reflectance standard $S_{ref}(\lambda)$ (defined as 100% at all wavelengths) where $\lambda$ represents wavelengths. The diffuse reflectance spectrum of the skin site, $R(\lambda)$, is then given by the measured signal from the site, $S(\lambda)$, corrected for the dark current and the reflectance standard:

$$R(\lambda) = \frac{S(\lambda) - D}{S_{ref}(\lambda) - D}$$

The apparent absorption spectrum $A(\lambda)$ can be calculated as the negative of the logarithm base 10 of $R(\lambda)$:

$$A(\lambda) = -\log_{10}[R(\lambda)]$$

Figure 17:
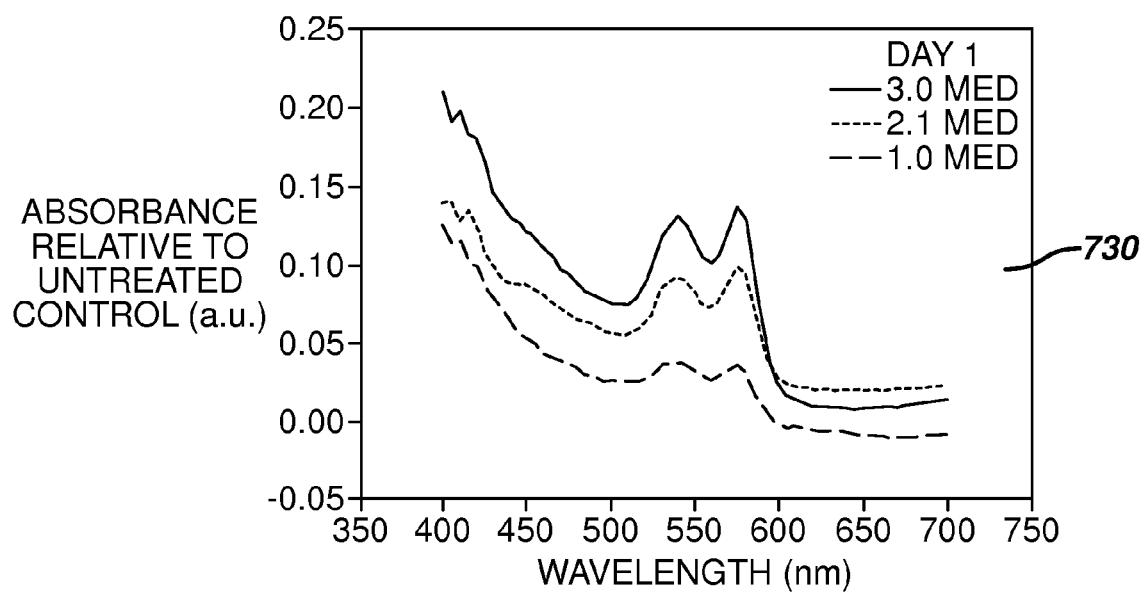
FIGS. 17 and 18 are exemplary graphs of data from diffuse reflectance spectroscopy.
Figure 18:
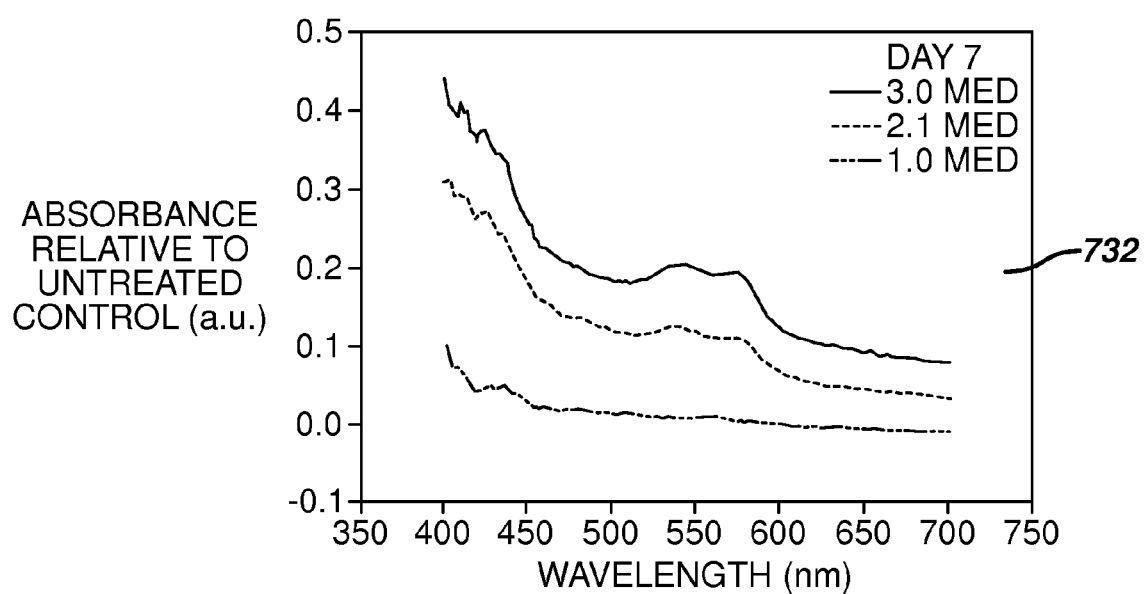

FIGS. 17 and 18 are graphs 730, 732 showing examples of DRS data obtained from skin in vivo on day 1 and 7 after exposure to 1.0, 2.1, and 3.0 times the minimal erythemogenic dose (MED) from FS-20 lamps. DRS measurements were taken with an Ocean Optics USB-2000 spectrophotometer. Graphs 730 and 732 show absorption spectra calculated based on the preceding equation.

Figure 19:
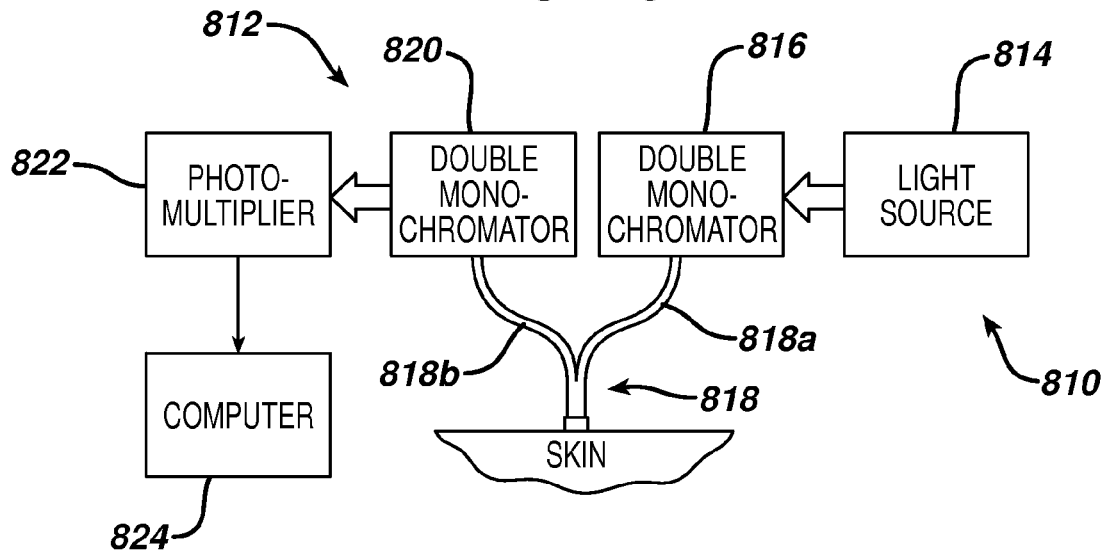
FIG. 19 is a diagram of a spectrometer for performing fluorescence spectroscopy.

FIG. 19 shows an apparatus 810 for performing fluorescence spectroscopy of the skin. The spectrofluorimeter 812 may be obtained from SPEX Industries (Horiba Group, Edison, N.J.) and includes a double monochromator-based fluorescence spectrometer with a xenon lamp as the excitation source 814. The radiation from the excitation source 814 is filtered by a double monochromator 816 and is focused into a quartz fiber bundle 818 with individual fiber diameters between 100 and 200 um. The distal end of the fiber bundle 818 is brought into contact with the skin sample under study. The delivery and collection fibers 818a, 818b are packed together in a random manner. Emitted radiation is collected by optical fibers of the bundle 818 and is analyzed by a double monochromator in the emission compartment 820. The intensity of the emitted radiation is measured by a photomultiplier (PMT) 822. The output of the PMT 822 is processed by a computer 824, which also controls the instrument. An important feature of the spectrofluorimeter 812 is the double monochromator design, which significantly improves the signal to noise ratio at short wavelengths ($\lambda$<300 nm).

Figure 20:
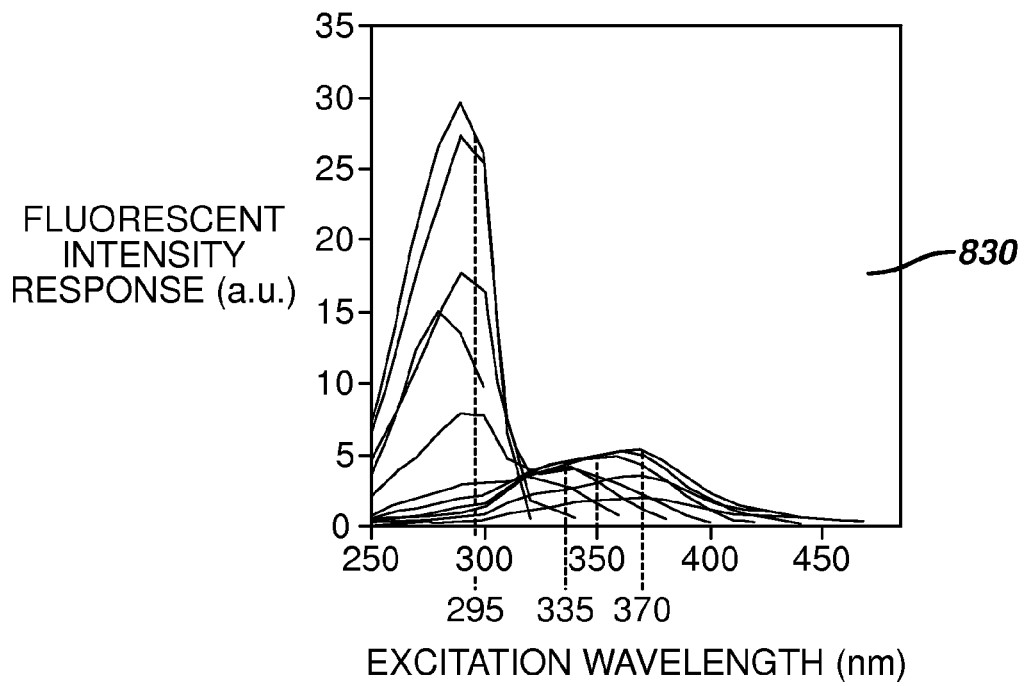
FIG. 20 is a graph showing data from fluorescence spectroscopy.

FIG. 20 shows a graph 830 of serial excitation spectra from the right cheek of a 27-year-old volunteer. The excitation wavelengths range from 250 to 470 nm in increments of 10 nm. For each spectrum, the excitation monochromator 816 was scanned from 250 to within 20 nm of the emission monochromator 820 setting. The emission wavelength of each scan was incremented by 20 nm form the previous starting at 280 nm. The major fluorescence peaks have been labeled with the corresponding excitation wavelength: (i) 295 nm excitation, due to trytophan fluorescence; (ii) 335 nm excitation, due to PDCCL; (iii) 350 nm excitation, possibly due to NADH; and (iv) 370 nm excitation, due to CDCCL.

It is understood that while the invention has been described in conjunction with the detailed description thereof, that the foregoing description is intended to illustrate and not limit the scope of the invention, which is defined by the scope of the appended claims. Other aspects, advantages, and modifications are within the scope of the claims.

What is claimed:

1. An apparatus for capturing data about a person's skin, comprising: a camera for capturing the images of the person; a display for displaying images captured by said camera; said display selectably displaying a real time image captured by said camera, means for illuminating permitting said camera to capture images under a plurality of lighting conditions, said images displayable on said display; probe means for measuring a predetermined parameter of the skin in a specific area, said probe means capturing skin data other than image data; and control means for controlling said camera, said probe means and said display for selectively capturing images of the person and skin data from said probe means and displaying the captured images and skin data on said display, said control means including a computer programmed to direct said camera and said means for illuminating to automatically sequentially capture a plurality of images using a plurality of different wavelengths of light, said real-time image allowing the person to visualize and interactively adjust the position of the probe means, before activating said probe means to capture skin data.

2. The apparatus of claim 1, wherein at least a portion of said real time image may be selectively enlarged.

3. The apparatus of claim 2, further including memory means for storing a plurality of images captured by said camera and skin data from said probe means, said control means controlling access to said plurality of images and skin data stored in said memory means and controlling display of said plurality of images and skin data on said display.

4. The apparatus of claim 3, wherein said display is a touch-screen display for displaying images captured by said camera, said touch-screen display capable of receiving input from an operator of the apparatus for controlling the review of captured images in conjunction with said control means.

5. The apparatus of claim 4, further including means for providing usage instructions to a user.

6. The apparatus of claim 5, wherein the instructions provided by said means for providing usage instructions enable a person having no training in the use of the apparatus to use it to capture and view images taken thereby and to operate said probe means.

7. The apparatus of claim 1, wherein said means for illuminating provides light selected from at least one of visible light, polarized light, ultraviolet light and blue light.

8. The apparatus of claim 2, wherein said selectively enlarged portion of said real-time image allows the person to visualize and interactively adjust the position of said probe means before activating said probe means to capture skin data.

9. The apparatus of claim 1, wherein said probe means includes at least one of a probe for measuring diffuse reflectance spectrum, fluorescent spectrum, infrared spectrum, conductivity, elastic modulus and moisturization.

10. The apparatus of claim 9, wherein said probe means includes a plurality of probes selectable by the user.

11. A method of capturing data about a person's skin, comprising the steps of: (A) providing an imaging station having, a camera, a light source, a display for displaying images captured by the camera; at least one non-imaging probe for measuring a parameter of the skin in a specific area, a controller with an operator interface; (B) positioning the person relative to the camera; (C) providing the person with the options of capturing images with the camera or obtaining skin data with the probe; (D) implementing the option selected in the prior step; (E) when the probe option is selected, displaying a real-time image of the user to allow the user to visualize and interactively adjust the position of the probe, enabling the probe and activating the probe to capture the skin data; (F) storing the data captured and; (G) selectively displaying the captured data on the display.

12. The method of claim 11, wherein during said step of displaying a real-time image, at least a portion of said real-time image may be selectively enlarged and wherein the step of implementing when the probe option is selected includes displaying the enlarged portion of the real-time image of the user to allow the user to visualize and interactively adjust the position of the probe.

13. The method of claim 12, wherein the imaging station has a plurality of sources of light of different wavelengths and the plurality of different images includes images captured with different wavelengths of light.

14. The method of claim 13, further comprising the step of repeating the steps of enabling the probe and activating the probe a selected number of times to capture additional data.

15. The method of claim 14, wherein the position of the probe on at least one occasion of activating is determined in reference to a photographic image of the person taken at a time removed from the time of activation.

16. The method of claim 14, wherein the probe is moved to at least one different position on the surface of the skin of the person between sequential steps of activation.

17. The method of claim 13, further comprising the step of providing instructions for self-use of the imaging/probe station to the user thereof in the form of at least one of text, graphics and auditory instructions.

18. A method for selectively capturing and viewing a plurality of digital images, comprising the steps of: (A) sequentially capturing a plurality of digital images by sequentially illuminating a subject with a plurality of different wavelengths of light and synchronously capturing the plurality of images during said step of sequentially illuminating; (B) storing the captured images; (C) displaying a plurality of the captured images as thumbnail images on a display; (D) selecting at least one of the thumbnail images for display at a larger scale on the display; (E) displaying a real time image of the person; (F) displaying a specific area of the skin captured in the selected image at the larger scale; (G) selecting a non-imaging probe for measuring a particular skin characteristic; (H) positioning the probe on the specific area of the skin guided by the real-time image; (I) activating the probe to capture the skin data; (J) storing the skin data; (K) displaying the skin data to the user.

* * * * *